(12) United States Patent
Liu et al.

(10) Patent No.: US 11,543,544 B2
(45) Date of Patent: *Jan. 3, 2023

(54) IMAGING SYSTEM AND METHOD FOR MAKING THE SAME

(71) Applicant: SHANGHAI UNITED IMAGING HEALTHCARE CO., LTD., Shanghai (CN)

(72) Inventors: Weiping Liu, Shanghai (CN); Guanghe Wu, Shanghai (CN); Shitao Liu, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 0 days.

This patent is subject to a terminal disclaimer.

(21) Appl. No.: 17/329,122

(22) Filed: May 24, 2021

(65) Prior Publication Data

US 2021/0293980 A1 Sep. 23, 2021

Related U.S. Application Data

(63) Continuation of application No. 15/171,846, filed on Jun. 2, 2016, now Pat. No. 11,016,204.

(30) Foreign Application Priority Data

Dec. 11, 2015 (CN) .......................... 201510922862.4
Feb. 3, 2016 (CN) .......................... 201610079034.3

(51) Int. Cl.
*A61B 6/03* (2006.01)
*G01T 1/29* (2006.01)
(Continued)

(52) U.S. Cl.
CPC .............. *G01T 1/2985* (2013.01); *A61B 6/03* (2013.01); *A61B 6/037* (2013.01); *G01T 1/1603* (2013.01);
(Continued)

(58) Field of Classification Search
CPC ............ A61B 6/03; A61B 6/032; A61B 6/037
See application file for complete search history.

(56) References Cited

U.S. PATENT DOCUMENTS 5,811,790 A 9/1998 Endo
6,025,598 A 2/2000 Tago
(Continued)

FOREIGN PATENT DOCUMENTS

CN 2873102 Y 2/2007
CN 201974530 U 9/2011
(Continued)

OTHER PUBLICATIONS

International Search Report in PCT/CN2016/105369 dated Feb. 8, 2017, 5 pages.
(Continued)

*Primary Examiner* — David P Porta
*Assistant Examiner* — Shun Lee
(74) *Attorney, Agent, or Firm* — Metis IP LLC

(57) ABSTRACT

An imaging system is provided. A method for installing the imaging system is provided. The imaging system may include a first modality imaging apparatus. The first modality imaging apparatus may have a detector including a scintillator unit, a photodetector unit, a circuit unit, a supporting block, and a supporting board. The supporting block may be disposed on an end of the scintillator unit. The supporting board may be disposed between the photodetector unit and the circuit unit.

20 Claims, 24 Drawing Sheets

(51) Int. Cl.
*G01T 1/20* (2006.01)
*G01T 7/00* (2006.01)
*G01T 1/16* (2006.01)
*G01T 1/164* (2006.01)
*A61B 6/00* (2006.01)

(52) U.S. Cl.
CPC .......... *G01T 1/1644* (2013.01); *G01T 1/2018* (2013.01); *G01T 7/00* (2013.01); *A61B 6/4241* (2013.01)

(56) References Cited

U.S. PATENT DOCUMENTS

| | | |
|---|---|---|
| 6,292,529 B1 | 3/2001 | Marcovici et al. |
| 2002/0070343 A1 | 6/2002 | Hoffman |
| 2002/0071523 A1 | 6/2002 | Busse et al. |
| 2003/0076925 A1 | 4/2003 | Desilets et al. |
| 2004/0072337 A1 | 4/2004 | Moon et al. |
| 2005/0027218 A1 | 2/2005 | Filtvedt et al. |
| 2007/0003021 A1 | 1/2007 | Guertin et al. |
| 2009/0121142 A1 | 5/2009 | Heismann et al. |
| 2009/0127466 A1 | 5/2009 | Chiyoma |
| 2010/0116996 A1 | 5/2010 | Poorter |
| 2011/0017916 A1 | 1/2011 | Schulz et al. |
| 2012/0153172 A1 | 6/2012 | Sumi |
| 2012/0273687 A1 | 11/2012 | Nariyuki et al. |
| 2013/0003932 A1 | 1/2013 | Nishino |
| 2014/0014843 A1 | 1/2014 | Ikeda et al. |
| 2014/0312238 A1 | 10/2014 | Liu et al. |
| 2014/0367577 A1 | 12/2014 | Badawi et al. |
| 2015/0073272 A1 | 3/2015 | Corbeil |
| 2015/0092906 A1 | 4/2015 | Liu et al. |
| 2015/0164448 A1 | 6/2015 | Liu et al. |

FOREIGN PATENT DOCUMENTS

| | | |
|---|---|---|
| CN | 102393529 A | 3/2012 |
| CN | 204520736 U | 8/2015 |
| CN | 104905811 A | 9/2015 |
| CN | 105360673 A | 3/2016 |
| CN | 105769230 A | 7/2016 |
| JP | H0651068 A | 2/1994 |
| JP | 2006255275 A | 9/2006 |
| JP | 2014035250 A | 2/2014 |

OTHER PUBLICATIONS

Written Opinion in PCT/CN2016/105369 dated Feb. 8, 2017, 6 pages.
First Office Action in Chinese Application No. 201610079034.3 dated Mar. 10, 2017, 14 pages.
First Office Action in Chinese Application No. 201510922862.4 dated Apr. 21, 2017, 13 pages.
Notice of Reasons for Refusal in Japanese Application No. 2017-534710 dated Sep. 3, 2018, 12 pages.
Notice of Reasons for Refusal in Japanese Application No. 2017-534710 dated Dec. 12, 2018, 7 pages.
General Electric Company, RTV Silicone Rubber Product Selector Guide, GE Advanced Materials, 2005, 32 pages.
A. G. Pickett et al., Handbook of Design Data on Elastomeric Materials Used In Aerospace Systems, Technical Report No. ASD-TR-61-234, 1962, 233 pages.

IMAGING SYSTEM AND METHOD FOR MAKING THE SAME

CROSS-REFERENCE TO RELATED APPLICATIONS

This application is a continuation of U.S. application Ser. No. 15/171,846, filed on Jun. 2, 2016, which claims priority of Chinese Patent Application No. 201510922862.4 filed on Dec. 11, 2015 and Chinese Patent Application No. 201610079034.3 filed on Feb. 3, 2016, the entire contents of each of which are hereby incorporated by reference.

TECHNICAL FIELD

This present disclosure relates to an imaging system, and more particularly, relates to a Positron Emission Tomography (PET) system and method for making the same.

BACKGROUND

Positron Emission Tomography (PET) has been widely used in medicine for diagnosis and other purposes, such as cancer diagnosis and management, cardiology and cardiac surgery, neurology and psychiatry, etc. In recent years, PET has also been used in multi-modality imaging system for generating high quality images, such as Positron Emission Tomography-Computed Tomography (PET-CT) and Positron emission tomography-magnetic resonance imaging (PET-MRI).

SUMMARY

In a first aspect of the present disclosure, an imaging system having a first modality imaging apparatus is provided. In some embodiments, the first modality imaging apparatus may have a detector. The detector may include a scintillator unit, a photodetector unit, a circuit unit, a supporting block, and a supporting board. In some embodiments, the detector may include a supporting block disposed on an end of the scintillator unit and a supporting board disposed between the photodetector unit and the circuit unit.

In a second aspect of the present disclosure, a multi-modality imaging system installation method is provided. The method may include one or more of the following operations. A first modality imaging apparatus having a first cavity and a first housing may be provided. A second modality imaging apparatus having a second cavity and a second housing may be provided. The first modality imaging apparatus may be seated. A supporting block may be installed in the first modality imaging apparatus. A first guiding block may be installed on the first housing of the first modality imaging apparatus and a second guiding block may be installed on the second housing of a second modality imaging apparatus, wherein the first guiding block and second guiding block may be configured to guide a second scanning cavity of the second modality imaging apparatus align with an axial direction of the first scanning cavity in an axial direction of the first scanning cavity.

In some embodiments, the detector may further include a shielded shell configured to contain the scintillator unit, the photodetector unit, the supporting board and the circuit unit.

In some embodiments, the supporting board may segment the shielded shell into a first cavity and a second cavity, wherein the scintillator unit and the photodetector unit may be disposed in the first cavity, and the circuit unit may be disposed in the second cavity.

In some embodiments, the supporting board may include a cooling channel configured to deliver a cooling medium.

In some embodiments, the detector may further include an elastic component disposed between the supporting board and the photodetector unit or disposed between the supporting board and the circuit unit.

In some embodiments, the elastic component may be a spring, an elastic cushion or an elastic board.

In some embodiments, the elastic component may have thermal conductance.

In some embodiments, the detectors may be configured to encircle a ring having an axis, wherein the distance between the supporting board and the axis of the ring is less than the distance between the circuit unit and the axis of the ring.

In some embodiments, the imaging system may further include a second modality apparatus and an installation apparatus. The installation apparatus may include a supporting block, a first guiding block, and a second guiding block.

In some embodiments, the first guiding block may be disposed on the first housing of the first modality imaging system and the second guiding block may be disposed on the second housing of the second modality imaging apparatus. In some embodiments, when the first guiding block aligns with the second guiding block, the second modality imaging apparatus may sit on the supporting block.

In some embodiments, the installation apparatus may further include a third guiding block having a first end and a second end, wherein the first end of the third guiding block may be connected to the first housing of the first modality imaging apparatus and the second end may be connected to the supporting block.

In some embodiments, the supporting block may include a first supporting plate and an adjustable bolt. In some embodiments, the adjustable bolt may be disposed on the first supporting plate and configured to adjust the height of the first supporting plate.

In some embodiments, the supporting block may further include a second supporting plate parallel to the first supporting plate. In some embodiments, the second supporting plate may be connected to the first supporting plate via a supporting lump.

In some embodiments, the supporting block may further include a guide rail and a slide lump. In some embodiments, the guide rail may be disposed on the first supporting plate and the slide lump may be fixed to the second supporting plate and configured to guide the second supporting plate to move on the guide rail.

In some embodiments, the supporting block may further include a limit lump disposed on the second supporting plate, wherein the second modality imaging apparatus may seat in the limit lump.

In some embodiments, the first guiding block and the second guiding block may each have an L-shape, wherein the first guiding block may further include a groove configured to indicate the alignment of the first guiding block and the second guiding block when the second guiding block is inserted into the groove.

In some embodiments, the first guiding block may be a light emission device and the second guiding block may be a light reception device.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of example in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

It will be understood that the term "system," "device," "apparatus," "unit," "module," "component," and/or "block" used herein are one method to distinguish different components, elements, parts, section or assembly of different level in ascending order. However, the terms may be exchanged or displaced by other expression if they may achieve the same purpose.

It will be understood that when a device, apparatus, unit, module, component or block is referred to as being "on," "connected to" or "coupled to" another device, apparatus, unit, module, component or block, it may be directly on, connected or coupled to, or communicate with the other device, apparatus, unit, module, component or block, or an intervening device, apparatus, unit, module, component or block may be present, unless the context clearly indicates otherwise. As used herein, the term "and/or" includes any and all combinations of one or more of the associated listed items.

The terminology used herein is for the purposes of describing particular examples and embodiments only, and is not intended to be limiting. As used herein, the singular forms "a," "an," and "the" may be intended to include the plural forms as well, unless the context clearly indicates otherwise. It will be further understood that the terms "include," and/or "comprise," when used in this disclosure, specify the presence of integers, devices, behaviors, stated features, steps, elements, operations, and/or components, but do not exclude the presence or addition of one or more other integers, devices, behaviors, features, steps, elements, operations, components, and/or groups thereof. It will be further understood that the terms "construction" and "reconstruction," when used in this disclosure, may represent a similar process in which an image may be transformed from data.

Figure 1:
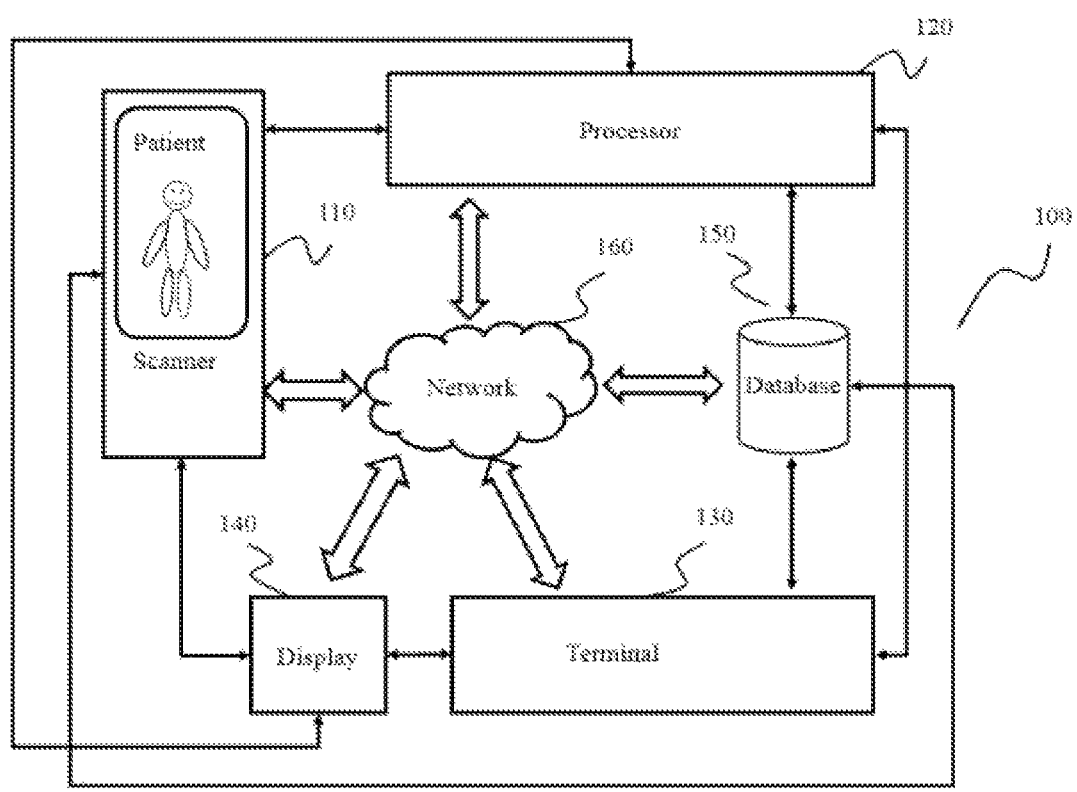
FIG. 1 is a block diagram of an imaging system according to some embodiments of the present disclosure.

FIG. 1 is a diagram of an imaging system 100 according to some embodiments of the present disclosure. It should be noted that the imaging system 100 described below is merely provided for illustration purposes, and not intended to limit the scope of the present disclosure. The imaging system may find its applications in different fields, for example, medicine, or industry. As another example, the system may be used in internal inspection of components including, e.g., flaw detection, security scanning, failure analysis, metrology, assembly analysis, void analysis, wall thickness analysis, or the like, or any combination thereof. As illustrated in FIG. 1, the imaging system 100 may include a scanner 110, a processor 120, a terminal 130, a display 140, a database 150, and a network 160.

The scanner 110 may be configured to acquire some data by scanning a subject. The subject used herein may be any substance, a tissue, an organ, an object, a body of interest, etc. The scanner 110 may include a Digital Subtraction Angiography (DSA) scanner, a Magnetic Resonance Angiography (MRA) scanner, a Computed Tomography Angiography (CTA) scanner, a Positron Emission Tomography (PET) scanner, a Single Photon Emission Computed Tomography (SPECT) scanner, a Computed Tomography (CT) scanner, a Digital Radiography (DR) scanner, a multi-modality scanner, or the like, or any combination thereof. Exemplary multi-modality scanner may include a Computed Tomography-Positron Emission Tomography (CT-PET) scanner, a Computed Tomography-Magnetic Resonance Imaging (CT-MM) scanner, a Positron Emission Tomography-Magnetic Resonance Imaging (PET-MM) scanner, a Digital Subtraction Angiography-Magnetic Resonance Imaging (DSA-MR) scanner etc.

The processor 120 may be configured to process the data acquired from the scanner 110. In some embodiments, the data may include a text, an image, a voice, a force, an instruction, an algorithm, a program, or the like, or any combination thereof. In some embodiments, the processor 120 may include one or more processors, one or more processing cores, one or more memories, and one or more electronics for image processing, or the like, or any combination thereof. Merely by way of example, the processor 120 may be a Central Processing Unit (CPU), an Application-Specific Integrated Circuit (ASIC), an Application-Specific Instruction-Set Processor (ASIP), a Graphics Processing Unit (GPU), a Physics Processing Unit (PPU), a Digital Signal Processor (DSP), a Field Programmable Gate Array (FPGA), a Programmable Logic Device (PLD), a Controller, a Microcontroller unit, a Processor, a Microprocessor, an ARM, or the like, or any combination thereof. In some embodiments, the processor 120 may access the database 150 for processing the data.

The terminal 130 may be configured to input or receive data to and/or from a user, the network 160, the database 150, the processor 120, the display 140, or the like, or any combination thereof. In some embodiments, the terminal 130 may include a user input, a controller, a processor, etc. For example, the user input may be a keyboard input, a mouse input, a touch screen input, a handwritten input, an image input, a voice input, an electromagnetic wave input, or the like, or any combination thereof. The controller may be configured to control the scanner 110, the processor 120, the display 140, or the database 150. The processor may be configured to process data acquired in the terminal 130. In some embodiments, the processor 120 and the terminal 130 may be integrated as one device. Merely by way of example, the terminal 130 may be a computer, a laptop, a Personal Digital Assistant (PDA), a mobile phone, a tablet computer, a portable device, or the like, or any combination thereof.

The display 140 may be configured to display processed data from the scanner 110, the processor 120, the terminal 130, or the network 140. The display 140 may be any displayable device. In some other embodiments, the terminal 130 and the display 140 may be integrated as one device to input data, output data, display data, and control the imaging system 100.

The database 150 may be configured to store data relating to the imaging system. In some embodiments, the data may include a text, an image, a voice, a force, an instruction, an algorithm, a program, or the like, or any combination thereof. Merely by way of example, the database 150 may be a memory. The memory may be a main memory or an assistant memory. The main memory may include a Random Access Memory (RAM), a Read Only Memory (ROM), a Complementary Metal Oxide Semiconductor Memory (CMOS), etc. The assistant memory may include a magnetic surface memory, a Hard Disk Drive (HDD), a floppy disk, a magnetic tape, a disc (CD-ROM, DVD-ROM, etc.), a USB Flash Drive (UFD), or the like, or any combination thereof.

The network 160 may be configured to connect one or more components of the imaging system 100. Merely by way of example, the network 160 may include a telecommunications network, a local area network (LAN), a Local Area Network (LAN), a Wireless Local Area Network (WLAN), a Metropolitan Area Network (MAN), a Wide Area Network (WAN), a Bluetooth, a ZigBee, a Near Field Communication (NFC), or the like, or any combination thereof. In some embodiments, the processor 120, the database 150, the display 140, or the terminal 130 may be disposed near to the scanner 110. For example, the scanner 110, the processor 120, the database 150, the display 140, or the terminal 130 may be connected with each other through some transmission medium. The transmission medium may include solid, liquid, gas, plasma, or the like, or any combination thereof. In some other embodiments, one or more of the above components may be remote from the scanner 110. Merely by way of example, the processor 120 and the database 150 may be implemented on a cloud platform. The cloud platform may be a cloud computing platform or a cloud storing platform. The type of the cloud platform may include a private cloud, a public cloud, a hybrid cloud, a community cloud, a distributed cloud, an inter-cloud, a multi-cloud, or the like, or any combination thereof. As another example, the display 140 and the terminal 130 may be operated by a remote system.

It should be noted that the above description is merely provided for the purposes of illustration, and not intended to limit the scope of the present disclosure. For persons having ordinary skills in the art, multiple variations and modifications may be made under the teachings of the present disclosure. For example, the imaging system 100 may include several processors, databases, displays, terminals when the scanner 110 is a multi-modality scanner. As another example, the display 140, the terminal 130, and the processor 120 may be integrated as one device. However, those variations and modifications do not depart from the scope of the present disclosure.

Figure 2:
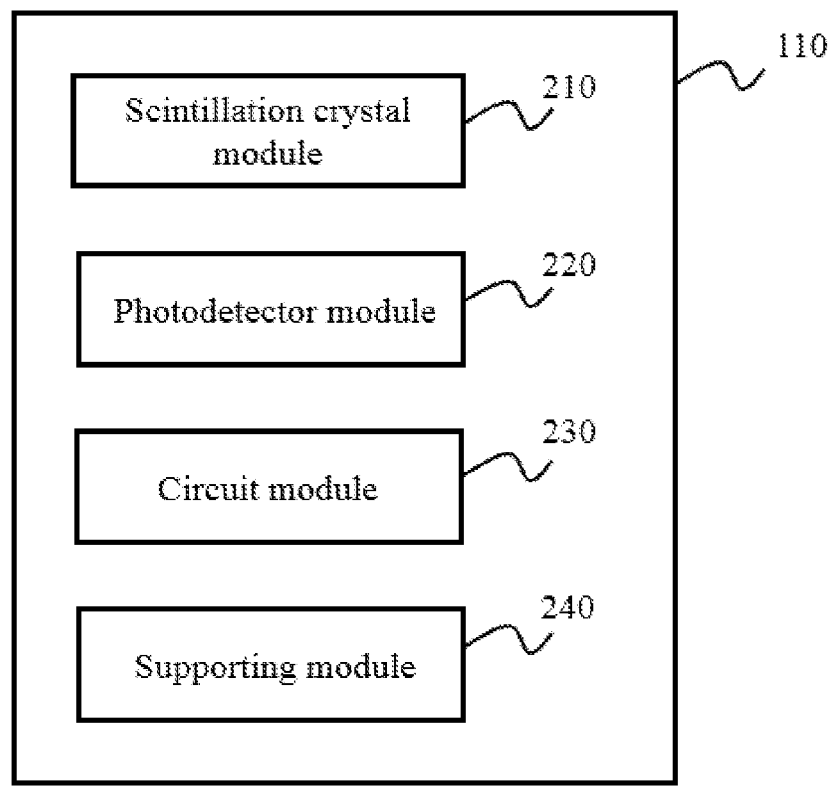
FIG. 2 is a block diagram of a scanner according to some embodiments of the present disclosure.

FIG. 2 is a block diagram of a scanner according to some embodiments of the present disclosure. As shown in the figure, the scanner 110 may include a scintillation crystal module 210, a photodetector module 220, a circuit module 230, and a supporting module 240.

The scintillation crystal module 210 may be configured to detect ionizing radiation to produce light photons. Exemplary scintillation crystal module 210 may include an organic crystal, a plastic scintillator, an inorganic crystal, a gaseous scintillator, a glass, or the like, or any combination thereof. In some embodiments, the organic crystal may include an anthracene ($C_{14}H_{10}$), a stilbene ($C_{14}H_{12}$), a naphthalene ($C_{10}H_8$), etc. In some embodiments, the organic liquid may be a liquid solution of one of more organic solutes in an organic solvent. Exemplary organic solutes may include a fluor such as p-terphenyl ($C_{18}H_{14}$), PBD ($C_{20}H_{14}N_2O$), butyl PBD ($C_{24}H_{22}N_2O$), PPO ($C_{15}H_{11}NO$), POPOP($C_{24}H_{16}N_2O$), or the like, or any combination thereof. Exemplary organic solvents may include toluene, xylene, benzene, phenylcyclohexane, triethylbenzene and decalin, or the like, or any combination thereof. In some embodiments, the plastic scintillator may include a fluor suspended in a matrix. Exemplary fluor may include polyphenyl hydrocarbons, oxazole and oxadiazole aryls, n-terphenyl (PPP), 2,5-diphenyloxazole (PPO), 1,4-di-(5-phenyl-2-oxazolyl)-benzene (POPOP), 2-phenyl-5-(4-biphenylyl)-1,3,4-oxadiazole (PBD), and 2-(4'-tert-butylphenyl)-5-(4"-biphenylyl)-1,3,4-oxadiazole (B-PBD), or the like, or any combination thereof. Exemplary matrices may include polymethylmethacrylate (PMMA), aromatic plastic, polyvinyl xylene (PVX) polymethyl, 2,4-dimethyl, 2,4,5-trimethyl styrenes, polyvinyl diphenyl, polyvinyl naphthalene, polyvinyl tetrahydronaphthalene, or the like, or any combination thereof. Exemplary inorganic crystals may include NaI(Tl), CsI(Tl), CsI(Na), CsI(pure), CsF, KI(Tl), LiI(Eu), $BaF_2$, $CaF_2(Eu)$, ZnS(Ag), $CaWO_4$, $CdWO_4$, YAG(Ce) ($Y_3Al_5O_{12}$ (Ce)), GSO, LSO, LYSO, BGO, MLS, or the like, or any combination thereof. In some embodiments, the gaseous scintillator may include nitrogen, helium, argon, krypton, xenon, helium and xenon, or the like, or any combination thereof. In some embodiments, the glass may include cerium-activated lithium, boron silicates, etc.

The photodetector module 220 may be configured to convert the light photons produced by the scintillation crystal module 210 into electrical signals. Exemplary photodetector module 220 may include a photomultiplier tube (PMT), an avalanche photodetector (APD), a position sensitive photodetector (PSPD), a position-sensitive APD (PSAPD), a silicon photomultiplier (SiPM), a position sensitive photomultiplier (PSPMT), a charge-sensitive preamplifier (CSP), a cadmium zinc telluride detector (CZT), or the like, or any combination thereof.

The circuit module 230 may be configured to process and readout the electrical signals produced by the photodetector module 220. For example, the circuit module 230 may amplify the electrical signals. As another example, the circuit module 230 may transmit data received from the photodetector module 220 to the network 160, the processor 120, the database 150, the display 140, or the terminal 130. Merely by way of example, the circuit module 230 may be a printed circuit board (PCB).

The supporting module 240 may be configured to improve compactness and firmness of the scanner 110. In some embodiments, the supporting module 240 may include a supporting block, a supporting board, a shielded shell, or an elastic component.

It should be noted that the above description is merely provided for the purposes of illustration, and not intended to limit the scope of the present disclosure. For persons having ordinary skills in the art, multiple variations and modifications may be made under the teachings of the present disclosure. For example, the supporting module 240 may be not included in the scanner 110 in some embodiments. As another example, the scanner 110 may include other components, e.g., an installation apparatus. However, those variations and modifications do not depart from the scope of the present disclosure.

Figure 3:
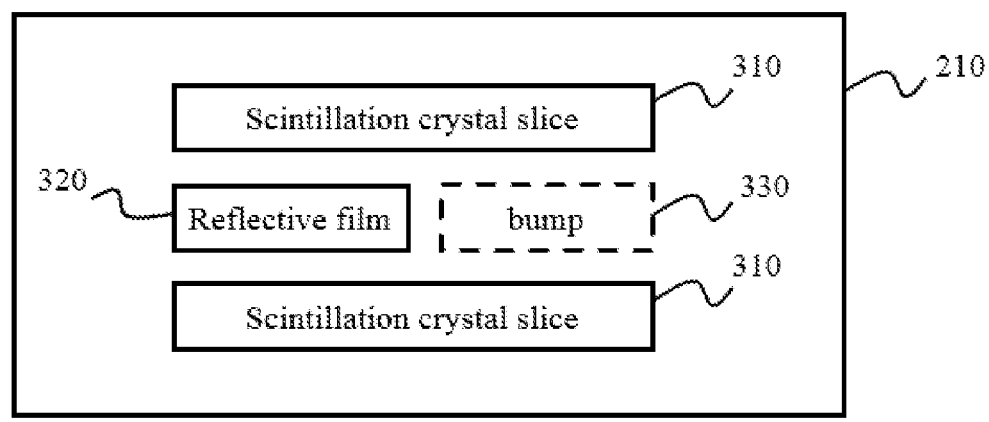
FIG. 3 is a block diagram of a scintillation crystal module according to some embodiments of the present disclosure.

FIG. 3 is a block diagram of the scintillation crystal module 210 according to some embodiments of the present disclosure. It should be noted that the scintillation crystal module 210 described below is merely provided for illustration purposes, and not intended to limit the scope of the present disclosure. As shown in FIG. 3, the scintillation crystal module 210 may include a plurality of scintillation crystal slices 310, at least one reflective film 320, and at least one bump 330. In some embodiments, the scintillation crystal slices 310 may be alternately stuck or glued to the at least one reflective film 320 to make the scintillation crystal module 210. In some other embodiments, the scintillation crystal module 210 may further include the least one bump 330 attached or glued to the at least one scintillation crystal slice 310.

Figure 4:
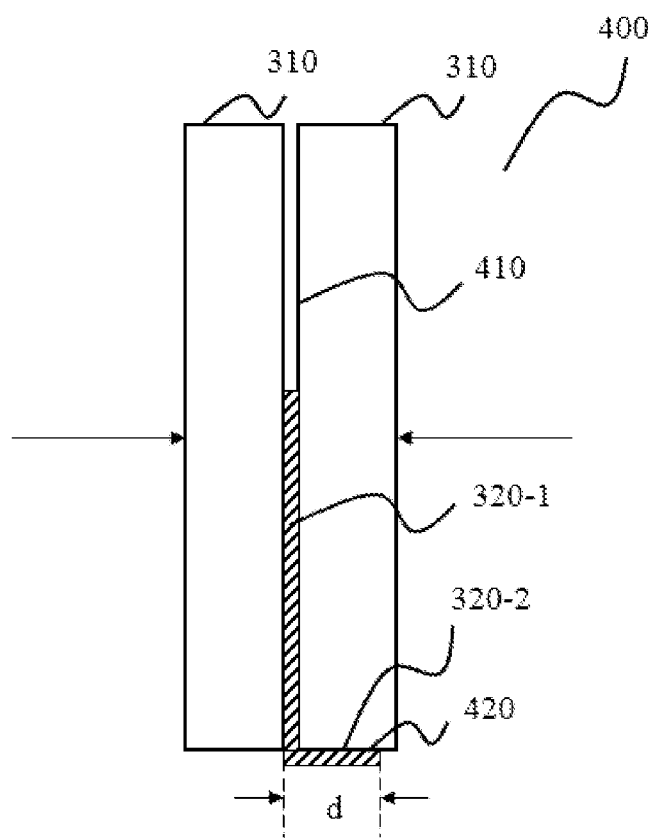
FIG. 4 is a section view of a scintillation crystal module according to some embodiments of the present disclosure.

FIG. 4 is a section view of a scintillation crystal module according to some embodiments of the present disclosure. For illustration purposes, FIG. 4 shows two scintillation crystal slices and one reflective film in a scintillation crystal module. It should be noted that the amount, size, or shape of one or both of the scintillation crystal slices and/or of the reflective film may be varied and not intended to limit the scope of the present disclosure. In some embodiments, the scintillation crystal module 400 may include at least one scintillation crystal slice 310 and at least one reflective film 320. The scintillation crystal slice 310 may include a side surface 410 and a bottom surface 420 essentially perpendicular to the side surface 410. The reflective film 320 may include a main portion 320-1 and a folded portion 320-2. In some embodiments, the main portion 320-1 and the folded portion may be an integral piece. In some embodiments, the folded portion 320-2 may be attached or connected to the main portion 320-1. The main portion 320-1 of the reflective film 320 may be stuck or glued to the side surfaces 410 between the two scintillation crystal slices 310 through an adhesive. Merely by way of example, the adhesive may be a liquid photosensitive curable adhesive (UV glue), a glass cement glue (silicone), etc. The folded portion 320-2 of the reflective film 320 may be pressed on the bottom surface 420 of the scintillation crystal slice 310. Merely by way of example, the length d of the folded portion 320-2 may range from 1.5 to 2.5 millimeters. The folded portion 320-2 may be underneath the bottom of the scintillation crystal module 400. The folded portion 320-2 may cover part of or the entire bottom of the scintillation crystal module 400.

In some embodiments, the scintillation crystal slices 310 and the reflective films 320 may be pressed by a press strip from four sides of the scintillation crystal module 400. The four sides of the scintillation crystal module 400 may include the front side, the back side, the left side, and the right side. The folded portion 320-2 or the corresponding bottom surface 420 may be parallel and level when the scintillation crystal module 400 is pressed. In some embodiments, the scintillation crystal module 400 may be cured after one or more of the four sides of the scintillation crystal module 400 are pressed. The adhesive on any one of the surfaces (e.g., six surfaces) of the scintillation crystal module 400 may be cleaned after curing. In some embodiments, the folded portion 320-2 may be removed. Merely by way of example, part of or the entire folded portion 320-2 may be removed by cutting using a tool.

In some embodiments, the scintillation crystal module 400 may be formed in various ways. For example, the folded portion 320-2 may contact the bottom surface 420 after the main portion 320-1 are stuck to a side surface 410, then the scintillation crystal module 400 may be formed. As another example, the main portion 320-1 and the folded portion 320-2 may form an integral piece; the main portion 320-1 may be firstly stuck to the side surfaces 410; then the remaining portion of the integral piece may be folded and/or pressed to the bottom surface 420 to form the folded portion 320-2.

In some embodiments, the size of the main portion 320-1 may be predetermined. For example, the size of the main portion 320-1 may be determined according to the size of the scintillation crystal module 210, or the size of a bottom surface 410 of a scintillation crystal slice 310. In some embodiments, the folded portion 320-2 and the main portion 320-1 may be an integral structure or in piece. There may be a crease mark between the folded portion 320-2 and the main portion 320-1. The crease mark may be a printed dotted line mark. The printed dotted line mark may be used for identification and/or positioning purposes when the main portion 320-1 and/or the folder portion 320-2 are stuck or glued to one or two of the scintillation crystal slices 310. In some embodiments, the folded portion 320-2 may be externally connected to the main portion 320-1.

In some embodiments, the side surface 410 of the scintillation crystal slice 310 may be a face to which the reflective film 320 sticks. In some embodiments, two relative large surfaces of the scintillation crystal slice 310 may be the side surfaces 410. The bottom surface 420 of the scintillation crystal slice 310 may be any one of the four surfaces that are essentially perpendicular to the side surface 410. In some embodiments, the bottom surface 420 of the scintillation crystal slice 310 may contact the folded portion 320-2 of the reflective film 320. The bottom surface 420 may be pressed on the surface of the folded portion 320-2 of the reflective film 320.

It should be noted that the above description is merely provided for the purposes of illustration, and not intended to limit the scope of the present disclosure. For persons having ordinary skills in the art, multiple variations and modifications may be made under the teachings of the present disclosure. For example, the adhesive may be another adhesive material suitable for making the scintillation crystal module 400. For another example, the bottom surface may not mean it is located at the bottom when the scintillation crystal module is in assembled into a detector. However, those variations and modifications do not depart from the scope of the present disclosure.

Figure 5:
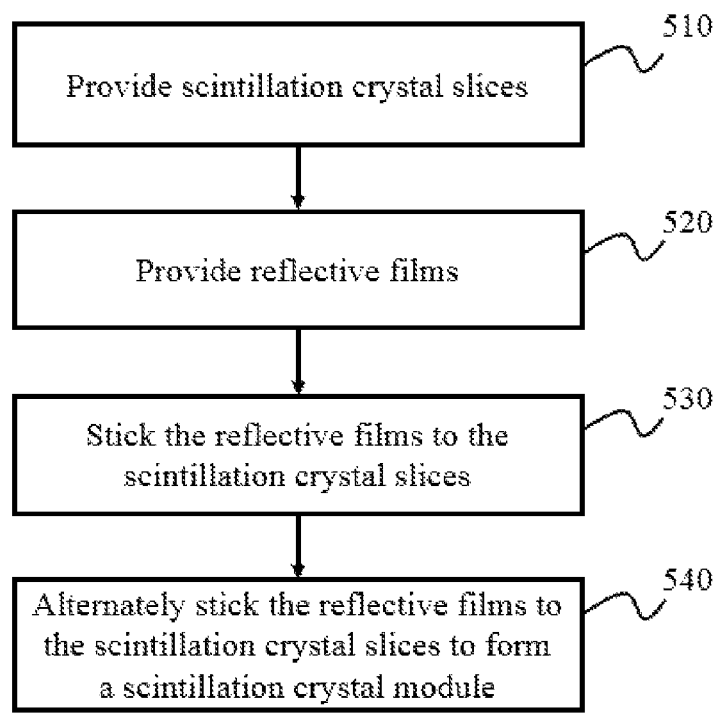
FIG. 5 illustrates an exemplary process for making a scintillation crystal module according to some embodiments of the present disclosure.

FIG. 5 illustrates an exemplary process for making the scintillation crystal module 400 according to some embodiments of the present disclosure. In step 510, at least one scintillation crystal slice 310 may be provided. The scintillation crystal slice 310 may include a side surface 410 and a bottom surface 420, wherein the bottom surface 420 may be perpendicular to the side surface 410. In step 520, at least one reflective film 320 may be provided. The reflective film may include a main portion 320-1 and a folded portion 320-2 connected to the main portion. In step 530, the reflective films 320 may be stuck or glued to the scintillation crystal slices 310. In some embodiments, the main portion 320-1 of the reflective films 320 may be stuck or glued to the side surface 410 of the scintillation crystal slices 310. In step 540, the reflective films 320 may be alternately stuck or glued to the scintillation crystal slices 310 to form the scintillation crystal module 400. In some embodiments, the folded portion 320-2 of the reflective films 320 may contact or otherwise be attached to the bottom surface 420 of the scintillation crystal slices 310.

In some embodiments, in step 530, the side surface 410 and the main portion 320-1 may first be gelatinized. For example, a liquid photosensitive curable adhesive may be gelatinized to the side surface 410 and the main portion 320-1. The crease mark between the folded portion 320-2 and the main portion 320-1 may be used for alignment. The crease mark may align with the edge of the side surface 410. The folded portion 320-2 may be folded along the crease mark and be pressed onto or otherwise attached to the bottom surface 420. Merely by way of example, the main portion 320-1 may be stuck to the side surface 410, and the folded portion 320-2 may be pressed onto the bottom surface 420, for example, essentially at the same time.

In some embodiments, in step 540, the reflective films 320 may be alternately stuck to the scintillation crystal slices 310 until a desired number of scintillation crystal slices are assembled to form a scintillation crystal module 400. For example, a scintillation crystal module 400 may include three scintillation crystal slices and two reflective films, or five scintillation crystal slices and four reflective films, or the like. In some embodiments, the scintillation crystal module 400 may be a sandwich structure.

It should be noted that the above description is merely provided for the purposes of illustration, and not intended to limit the scope of the present disclosure. For persons having ordinary skills in the art, multiple variations and modifications may be made under the teachings of the present disclosure. For example, one or more of steps in FIG. 5 may be omitted or repeated to form a scintillation crystal module 400. However, those variations and modifications do not depart from the scope of the present disclosure.

Figure 6A:
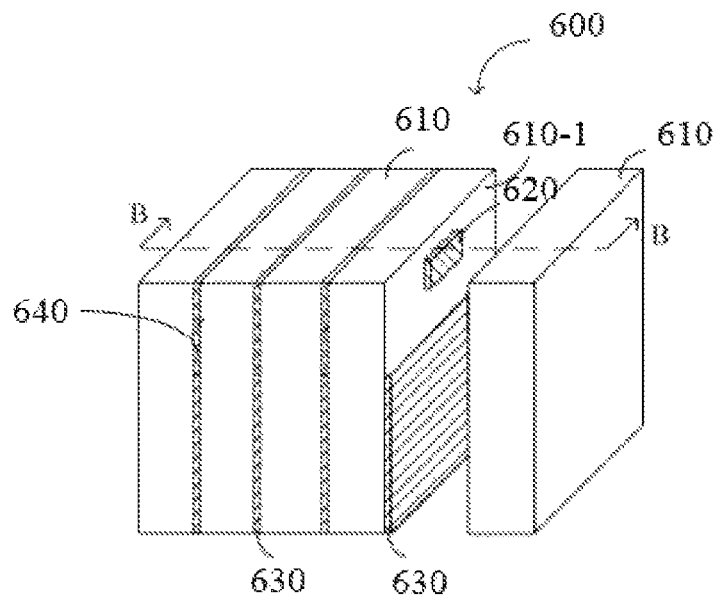
FIG. 6A shows a schematic view of a scintillation crystal module according to some embodiments of the present disclosure.

FIG. 6A shows a schematic view of a scintillation crystal module according to some embodiments of the present disclosure. In some embodiments, the scintillation crystal module 600 may include at least one first scintillation crystal slice 610, at least one reflective film 630, at least one bump 620, and an adhesive 640. The first scintillation crystal slice 610 may include a side surface 610-1. The bump 620 may be disposed on the side surface 610-1. In some embodiments, the thickness of the bump 620 may be essentially equal to the thickness of the reflective film 630. For instance, the thickness of the bump 620 may be between approximately 70% and approximately 75% of the thickness of the reflective film 630, or between approximately 75% and approximately 80% of the thickness of the reflective film 630, or between approximately 90% and approximately 95% of the thickness of the reflective film 630, or between approximately 95% and or approximately 100% of the thickness of the reflective film 630, or between approximately 100% and approximately 105% of the thickness of the reflective film 630, or between approximately 105% and approximately 110% of the thickness of the reflective film 630, or between approximately 70% and approximately 130% of the thickness of the reflective film 630, or between approximately 80% and approximately 120% of the thickness of the reflective film 630, or the like. The bump 620 may provide mechanical support to maintain the space between two scintillation crystal slices 610. The first scintillation crystal slice 610 may be stuck or glued to the reflective film 630 through the adhesive 640 on the side surface 610-1. In some embodiments, the first scintillation crystal slices 610 may be alternately stuck or glued to the reflective films 630 through the adhesive 640 to form the scintillation crystal module 600 including a desired number of layers. Then the adhesive 640 may be cured, and the first scintillation crystal slices 610 may be pressed to make the scintillation crystal module 600. In some embodiments, the structure of the scintillation crystal module 600 may be a sandwich. In some embodiments, one or both of the side surface 610-1 and the reflective film 630 may be pre-processed by gelatinization before they are stuck or glued.

In some embodiments, the bump 620 may be made by gelatinizing a liquid adhesive to the side surface 610-1, and curing the liquid adhesive. In some embodiments, the bump 620 may be processed by other methods. In some embodiments, the liquid adhesive may be same as the adhesive 640 for sticking or gluing the reflective film 630 onto the bottom surface 610-1.

Figure 6B:
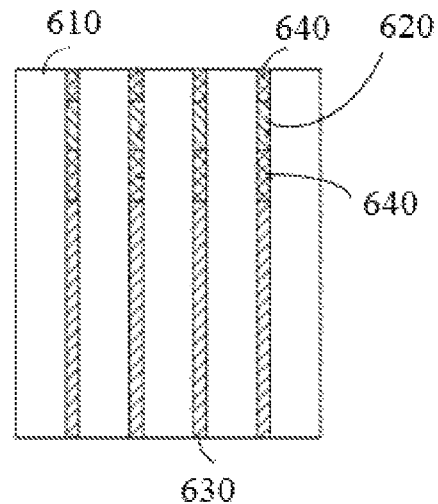
FIG. 6B shows a section view along the B-B direction of a scintillation crystal module according to some embodiments of the present disclosure.

As illustrated in FIG. 6A and FIG. 6B, the reflective film 630 may be stuck or glued to the lower portion of the side surface 610-1 of the first scintillation crystal slices 610. The bump 620 may be located at the upper portion of the side surface 610-1. The bump 620 may be disposed above the reflective film 630. The adhesive 640 may fill the gap between the two adjacent first scintillation crystal slices 610 except for the space occupied by the bump 620 and the reflective film 630. In some embodiments, the size (e.g., the area, the length of one or more dimensions, etc.) of the side surface 610-1 may be bigger than the reflective film 630. For example, the height of the side surface 610-1 may be bigger than that of the reflective film 630.

It should be noted that the above description is merely provided for the purposes of illustration, and not intended to limit the scope of the present disclosure. For persons having ordinary skills in the art, multiple variations and modifications may be made under the teachings of the present disclosure. For example, the thickness of the bump 620 and the reflective films 630 may have an error range, such as ±0.01 millimeters. As another example, the positions of the lower portion and the upper portion of the side surface 610-1 described above may be relative. The bump 620 and the reflective films 630 may be disposed at any other positions of the scintillation crystal slice 610 in other embodiments. Moreover, the upper portion or the lower portion of the side area 610 does not indicate the positions when the scintillation crystal module 600 is placed in a PET scanner or when the PET scanner is in operation. However, those variations and modifications do not depart from the scope of the present disclosure.

Figure 6C:
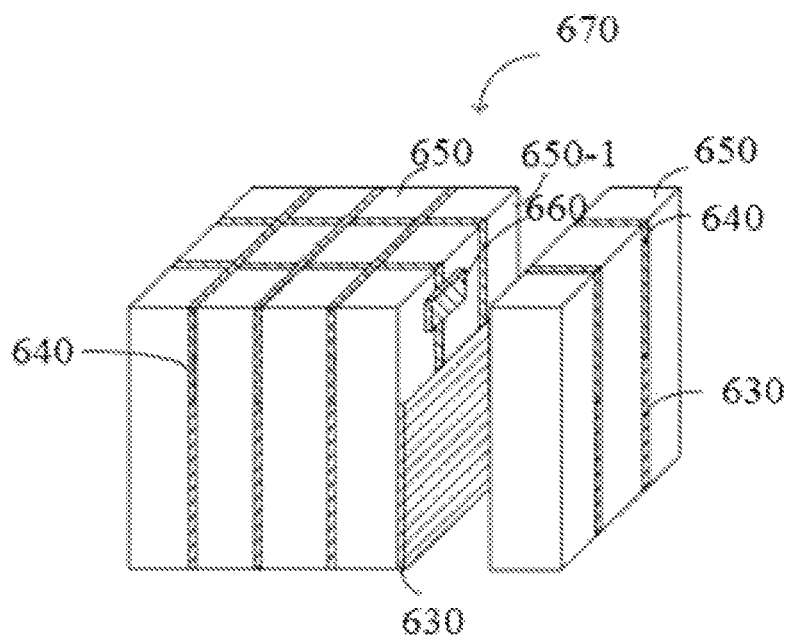
FIG. 6C shows a schematic view of a scintillation crystal array according to some embodiments of the present disclosure.

In some embodiments, the scintillation crystal module 600 may be cut into at least one scintillation crystal slices parallel to the B-B direction. FIG. 6C shows a schematic view of a scintillation crystal array 670 according to some embodiments of the present disclosure. In some embodiments, the scintillation crystal array 670 may include at least one second scintillation crystal slice 650, at least one reflective film 630, at least one bump 660, and an adhesive 640. The second scintillation crystal slice 650 may include a side surface 650-1. The bump 660 may be disposed on the side surface 650-1. In some embodiments, the thickness of the bump 660 may be essentially equal to the thickness of the reflective film 630. For instance, the thickness of the bump 660 may be between approximately 70% and approximately 75% of the thickness of the reflective film 630, or between approximately 75% and approximately 80% of the thickness of the reflective film 630, or between approximately 90% and approximately 95% of the thickness of the reflective film 630, or between approximately 95% and or approximately 100% of the thickness of the reflective film 630, or between approximately 100% and approximately 105% of the thickness of the reflective film 630, or between approximately 105% and approximately 110% of the thickness of the reflective film 630, or between approximately 70% and approximately 130% of the thickness of the reflective film 630, or between approximately 80% and approximately 120% of the thickness of the reflective film 630, or the like. The bump 660 may provide mechanical support to maintain the space between two scintillation crystal slices 650. In some embodiments, the second scintillation crystal slices 650 may be alternately stuck or glued to the reflective films 630 through the adhesive 640 to form a preliminary scintillation crystal array including a desired number of layers. Then the adhesive 640 may be cured, and the scintillation crystal slices 670 may be pressed to make the scintillation crystal array 670. In some embodiments, the structure of the scintillation crystal array 670 may be a sandwich. In some embodiments, one or both of the side surface 650-1 and the reflective film 630 may be gelatinization before they are stuck or glued.

In some embodiments, the bump 660 may be made by gelatinizing a liquid adhesive to the side surface 650-1, and curing the liquid adhesive. In some embodiments, the bump 660 may be processed by other methods. In some embodiments, the liquid adhesive may be same as the adhesive 640 for sticking or gluing the reflective film 630 onto the bottom surface 650-1.

In some embodiments, the reflective film 630 may be stuck or glued to the lower portion of the side surface 650-1 of the second scintillation crystal slices 650. The bump 660 may be located at the upper portion of the side surface 650-1. The bump 660 may be disposed above the reflective film 630. The adhesive 640 may fill the remaining space between the adjacent two second scintillation crystal slices 650 except for the space occupied by the bump 660 and the reflective film 630. In some embodiments, the size (e.g., the area, the length of one or more dimensions, etc.) of the side surface 650-1 may be bigger than the reflective film 630. For example, the height of the pates face 650-1 may be bigger than that of reflective film 630.

It should be noted that the above description is merely provided for the purposes of illustration, and not intended to limit the scope of the present disclosure. For persons having ordinary skills in the art, multiple variations and modifications may be made under the teachings of the present disclosure. For example, the thickness of the bump 660 and the reflective films 630 may have a reasonable error range, such as ±0.01 millimeters. As another example, the positions of the lower portion and upper portion of the side surface 650-1 described above may be relative. The bump 660 and the reflective films 630 may be disposed at any other positions of the scintillation crystal slice 650. Moreover, the upper portion or the lower portion of the side area 650 does not indicate the positions when the scintillation crystal module 600 is placed in a PET scanner or when the PET scanner is in operation. However, those variations and modifications do not depart from the scope of the present disclosure.

Figure 7:
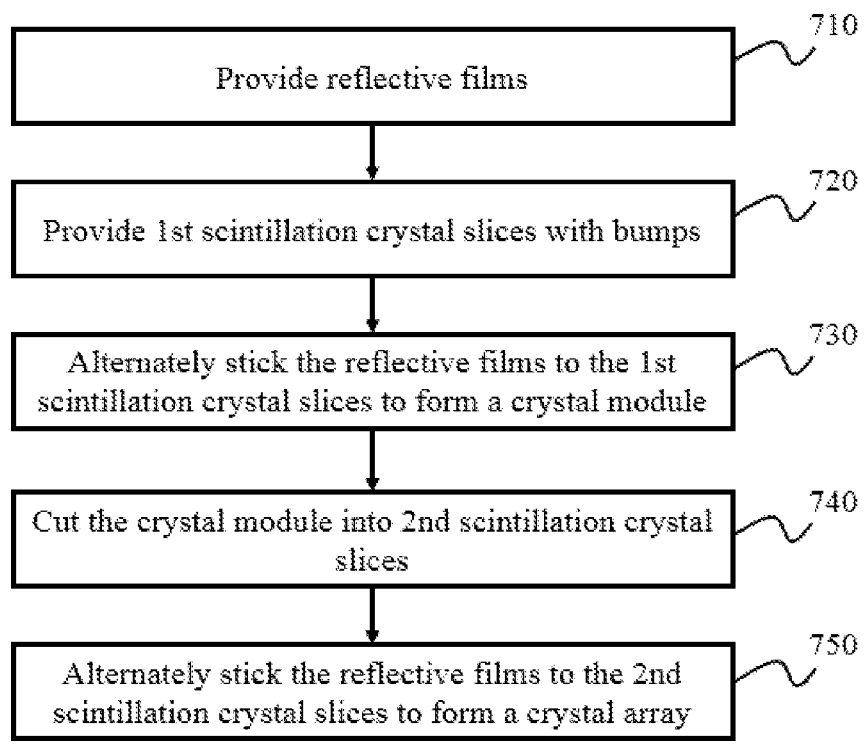
FIG. 7 illustrates an exemplary process for making the scintillation crystal array according to some embodiments of the present disclosure.

FIG. 7 illustrates an exemplary process for making a scintillation crystal array according to some embodiments of the present disclosure. In step 710, at least one reflective film 630 may be provided. In step 720, at least one first scintillation crystal slice 610 may be provided. The first scintillation crystal slice 610 may include a side surface 610-1. A bump 620 may be disposed on the side surface 610-1. In some embodiments, the thickness of the bump 620 may be essentially equal to the thickness of the reflective film 630.

In step 730, the reflective films 630 may be alternately stuck or glued to the first scintillation crystal slices 610 to form a scintillation crystal module 600. In some embodiments, the side surface 610-1 and the reflective film 630 may be gelatinization before being stuck or glued. There may be an interval between the bump 620 and the reflective film 630. In some embodiments, the first scintillation crystal slices 610 and the reflective films 630 may be cured to form the scintillation crystal module 600.

In step 740, the scintillation crystal module 600 may be cut into at least one second scintillation crystal slice 650 along the direction perpendicular to the side surface 610-1. The second scintillation crystal slice 650 may include a side surface 650-1. A bump 660 may be set on the side surface 650-1. In some embodiments, the thickness of the bump 660 may be essentially equal to the thickness of the reflective film 630.

In step 750, the reflective films 630 may be alternately stuck or glued to the second scintillation crystal slices 650 to form a scintillation crystal array 670. In some embodiments, the side surface 650-1 and the reflective film 630 may be pre-processed by gelatinizing before being stuck or glued. There may be an interval between the bump 660 and the reflective film 630. In some embodiments, the second scintillation crystal slices 650 and the reflective films 630 may be cured to form the scintillation crystal array 670.

It should be noted that the above description is merely provided for the purposes of illustration, and not intended to limit the scope of the present disclosure. For persons having ordinary skills in the art, multiple variations and modifications may be made under the teachings of the present disclosure. For example, one or more of steps in FIG. 7 may be omitted or repeated to form a scintillation crystal array 670. As another example, the order of some steps may be exchanged. However, those variations and modifications do not depart from the scope of the present disclosure.

Figure 8:
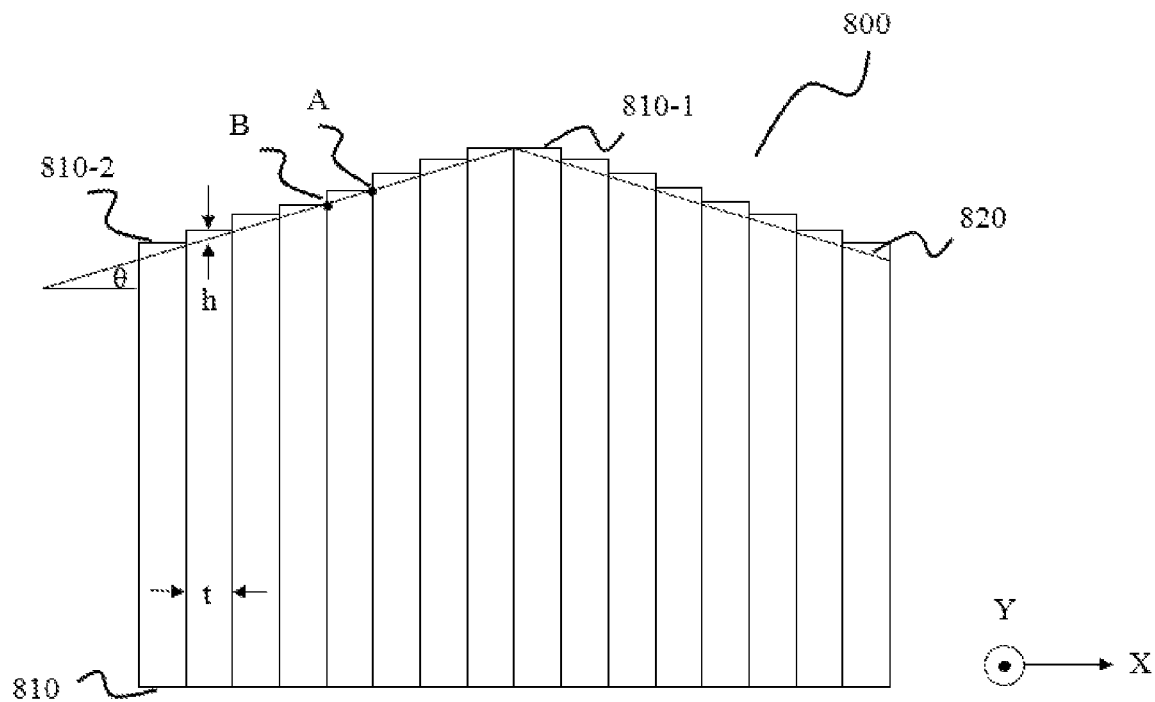
FIG. 8 is a section view of a scintillation crystal array according to some embodiments of the present disclosure.

FIG. 8 is a section view of a scintillation crystal array 800 according to some embodiments of the present disclosure. The scintillation crystal array 800 may include at least one scintillation crystal unit 810 and an inclined plane 820. The height of the scintillation crystal unit 810 may vary along with the inclined plane 820. The heights of some of the scintillation crystal units 810 may be different from each other in the first direction (the X direction in FIG. 8). In some embodiments, the heights of the scintillation crystal units 810 may be designed based on the inclined plane 820. In some embodiments, the heights of some of the scintillation crystal units 810 may be the same. Merely by way of example, the height of the scintillation crystal unit 810 at a position of along the inclined plane 820 may be determined according to a maximum height of the scintillation crystal array 800 at that position. The maximum height of the scintillation crystal array 800 at a position may be determined according to the inclined plane 820.

In some embodiments, the scintillation crystal unit 810 may be a scintillation crystal slice, a scintillation crystal stick, etc. The size or shape of the scintillation crystal unit 810 in the scintillation array 800 may be essentially the same or different. Merely by way of example, scintillation crystal slices may be generated by cutting the scintillation crystal module along a first direction. The scintillation crystal module may be cut along the first direction for multiple times to generate multiple scintillation crystal slices. The sizes of the multiple scintillation crystal slices may be essentially the same, or different. For instance, the cuts along the first direction may be essentially equal-distanced such that the thicknesses of the scintillation crystal slices are essentially the same. The thickness of a scintillation slice may refer to the dimension generated by two consecutive operations (e.g., cuts, etc.) along the first direction. Merely by way of example, the variation of the thicknesses of the scintillation crystal slices in the scintillation module may be within 2%, or 5%, or 8%, or 10% of the average thickness of the scintillation crystal slices.

A scintillation crystal stick may be generated by cutting the scintillation crystal slice along a direction different from the first direction. For instance, the second direction may be essentially perpendicular to the first direction. Merely by way of example, the angle between the first direction and the second direction may be between approximately 70° and approximately 75°, or between approximately 75° and approximately 80°, or between approximately 80° and approximately 85°, or between approximately 85° and approximately 90°, or between approximately 90° and approximately 95°, or between approximately 95° and approximately 100°, or between approximately 100° and approximately 105°, or between approximately 70° and approximately 120°, or between approximately 80° and approximately 110°, or between approximately 85° and approximately 95°. The scintillation crystal slices may be cut along the second direction for multiple times to generate multiple scintillation crystal sticks. The sizes of the multiple scintillation crystal sticks may be essentially the same, or different. For instance, the cuts along the second direction may be essentially equal-distanced such that the thickness of the scintillation crystal sticks are essentially the same. Merely by way of example, the variation of the thicknesses of the scintillation crystal slices in the scintillation module may be within 2%, or 5%, or 8%, or 10% of the average thickness of the scintillation crystal slices. The thickness of a scintillation crystal stick may refer to the dimension of the scintillation crystal stick generated by two consecutive operations (e.g., cuts, etc.) along the second direction. The thickness of a scintillation stick may be the same as the thickness of the scintillation crystal slice on the basis of which the scintillation crystal stick is generated by, for example, cutting.

For illustration purposes, the height of the scintillation crystal unit 810 may be described below. As shown in FIG. 8, the scintillation crystal array 800 may have a maximum height and a minimum height. The scintillation crystal array 800 may include a scintillation crystal unit 810-1 and a scintillation crystal unit 810-2. The height of the scintillation crystal unit 810-1 may be determined according to the maximum height of the scintillation crystal array 800. The height of the scintillation crystal unit 810-2 may be determined according to the minimum height of the scintillation crystal array 800. In some embodiments, the inclined plane 820 may be determined according to the position of the scintillation crystal module and the optical amplifier (not shown in the figure). A height difference h of two adjacent scintillation crystal units 810 may be determined according to an angle θ and a thickness t of the scintillation crystal unit 810. The angle θ may be an angle between the inclined plane 820 and the X direction. The height difference h may be determined according to an equation below:

$$h = t * tg\theta. \tag{Equation 1}$$

In some embodiments, the length of the scintillation crystal unit 810 along the Y direction may be essentially the same. Y is a direction perpendicular to the paper as illustrated in FIG. 8. The length of the scintillation crystal unit 810 may be essentially equal to the length of the scintillation crystal array 800 along the Y direction. In some embodiments, the thickness t of the scintillation crystal unit 810 may be essentially the same. For instance, the thickness t may be essentially equal to the ratio of the length of the scintillation crystal array 800 along the X direction to the number of the scintillation crystal unit 810 along the X direction. As used herein, "essentially," as in "essentially equal," "essentially the same," "essentially coincide with," "essentially parallel to," etc., with respect to a parameter or a characteristic may indicate that the variation is within 2%, or 5%, or 8%, or 10%, or 15% of the parameters or the characteristic, or an average value of the parameter in, for example, a scintillation crystal array or a scintillation crystal module, etc. In some embodiments, the lengths and/or the thicknesses of at least some scintillation crystal units 810 of the scintillation crystal array 800 may be different.

As shown in FIG. 8, scintillation crystal units 810 with different heights may generate one or more ladder inflection points, such as A and B. A line may be determined by the inflection points A and B. The line may essentially coincide with the inclined plane 820.

In some embodiments, the shape of the scintillation crystal array 800 may be a prism. Merely by way of example, the shape of the scintillation crystal array 800 may be a quadrangular prism.

It should be noted that the above description is merely provided for the purposes of illustration, and not intended to limit the scope of the present disclosure. For persons having ordinary skills in the art, multiple variations and modifications may be made under the teachings of the present disclosure. For example, the height of the scintillation crystal unit 810 may be designed by some other methods, or be assigned a random value. As another example, the thicknesses of at least some scintillation crystal units of the scintillation crystal array may be different. However, those variations and modifications do not depart from the scope of the present disclosure.

Figure 9:
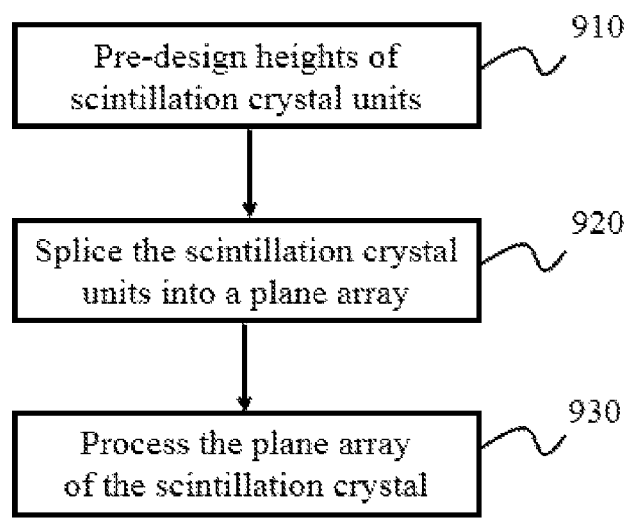
FIG. 9 illustrates an exemplary process for making a scintillation crystal array according to some embodiments of the present disclosure.

FIG. 9 illustrates an exemplary process for making the scintillation crystal array 800 according to some embodiments of the present disclosure. In step 910, the height of a scintillation crystal unit 810 may be designed. In some embodiments, at least two of scintillation crystal units 810 may have different heights. The height of the scintillation crystal unit 810 at a position or the height difference between adjacent scintillation crystal units 810 may be determined according to the inclined plane 820 of the scintillation crystal array 800.

In step 920, the scintillation crystal units 810 may be spliced together to form the scintillation crystal array 800. In some embodiments, the scintillation crystal units 810 may be spliced together by using optical coupling agent, coating, adhesive, reflective agent, or the like, or any combination thereof. In some embodiments, the splicing process may be same as making scintillation crystal module as described elsewhere in the present disclosure.

In step 930, the scintillation crystal array 800 may be processed to generate the inclined plane 820. In some embodiments, the processing method may include grinding, cutting, polishing, cleaning, carving, or the like, or any combination thereof.

In some embodiments, step 930 for processing the scintillation crystal array 800 may be executed before step 920. The splicing the scintillation crystal units 810 may be the last step to form the final scintillation crystal array 800.

It should be noted that the above description is merely provided for the purposes of illustration, and not intended to limit the scope of the present disclosure. For persons having ordinary skills in the art, multiple variations and modifications may be made under the teachings of the present disclosure. For example, one or more of steps in FIG. 9 may be omitted or repeated to form a scintillation crystal array 800. As another example, the inclined plane 820 may be formed according to other methods (e.g., eroding, etc.) to form a scintillation crystal array 800. However, those variations and modifications do not depart from the scope of the present disclosure.

Figure 10A:
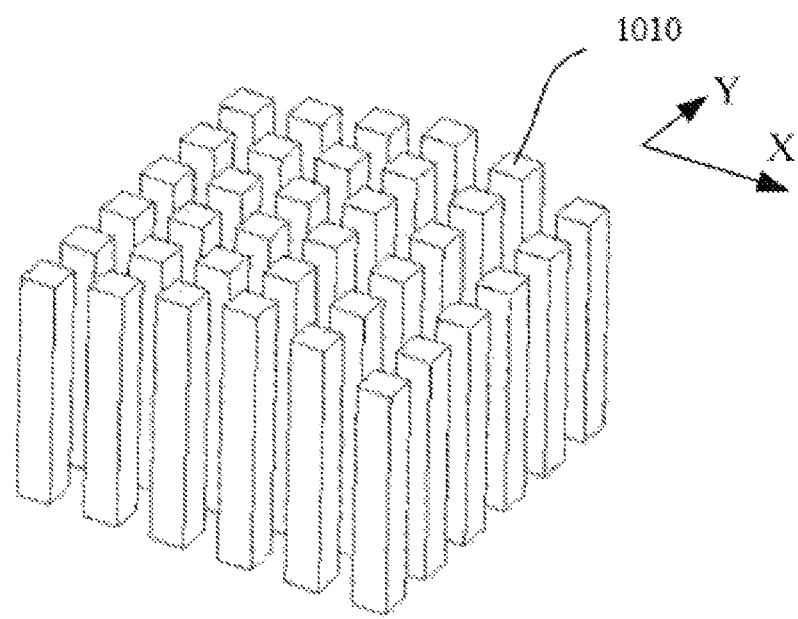
FIG. 10A-FIG. 10C illustrate an exemplary process for making a scintillation crystal array according to some embodiments of the present disclosure.
Figure 10B:
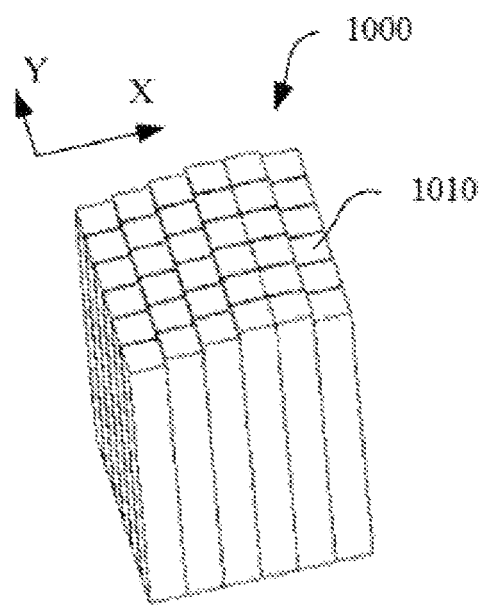
Figure 10C:
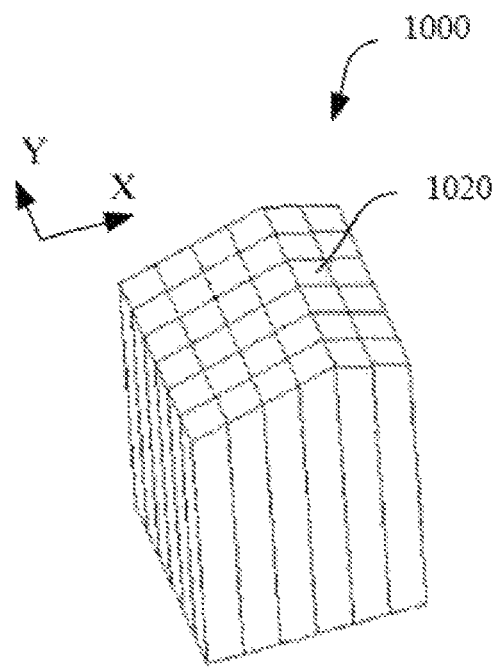

FIG. 10A through FIG. 10C illustrate an exemplary process for making a scintillation crystal array 1000 according to some embodiments of the present disclosure. The scintillation crystal array 1000 may include a plurality of scintillation crystal sticks 1010 as shown in FIG. 10C. As shown in FIG. 10A, a plurality of scintillation crystal sticks 1010 may be provided. The heights of the scintillation crystal sticks 1010 along the X direction may be designed according to an inclined plane 1020. For example, at least two of the scintillation crystal sticks 1010 along the X direction may have different heights. The heights of the scintillation crystal sticks 1010 along the Y direction may be essentially the same. As shown in FIG. 10B, the scintillation crystal sticks 1010 may be spliced together in both the X direction and the Y direction to form the scintillation crystal array 1000. The scintillation crystal array 1000 may be further processed to form the inclined plane 1020 as shown in FIG. 10C. In some embodiments, the processing method may include grinding, cutting, polishing, cleaning, carving, or the like, or any combination thereof.

FIG. 11A through FIG. 11E illustrate an exemplary process for making a scintillation crystal array 1100 according to some embodiments of the present disclosure. The scintillation crystal array 1100 may include a plurality of first scintillation crystal slices 1110, a plurality of second scintillation crystal slices 1130, and a plurality of scintillation crystal sticks 1140. The scintillation crystal array 1100 may have an inclined plane 1150.

Figure 11A:
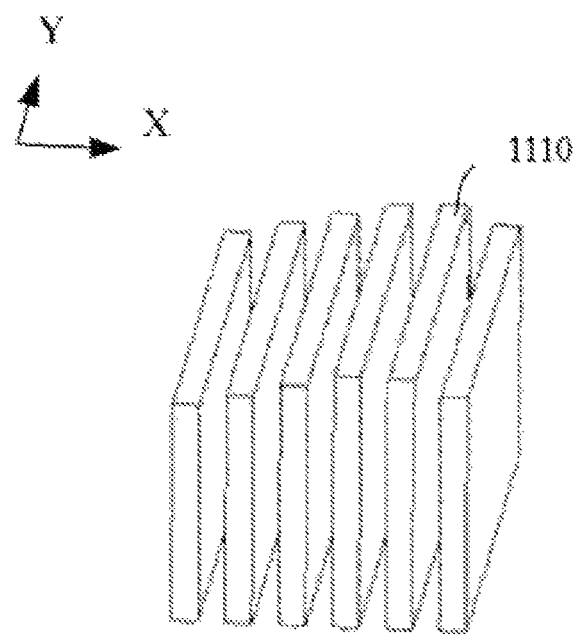
FIG. 11A-FIG. 11E illustrate an exemplary process for making a scintillation crystal array according to some embodiments of the present disclosure.
Figure 11B:
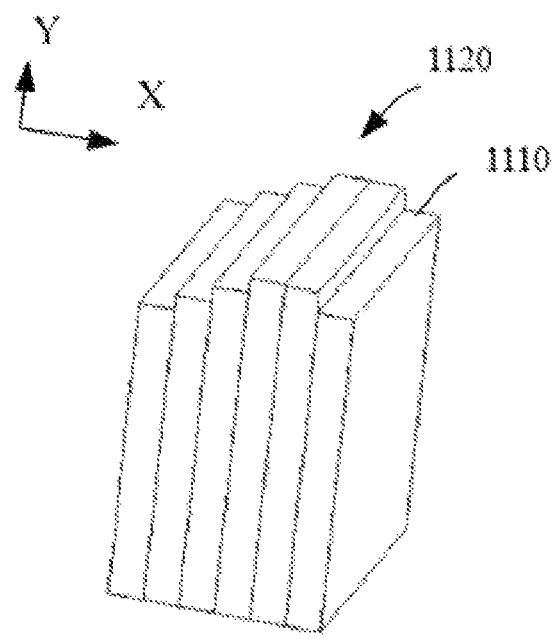
Figure 11C:
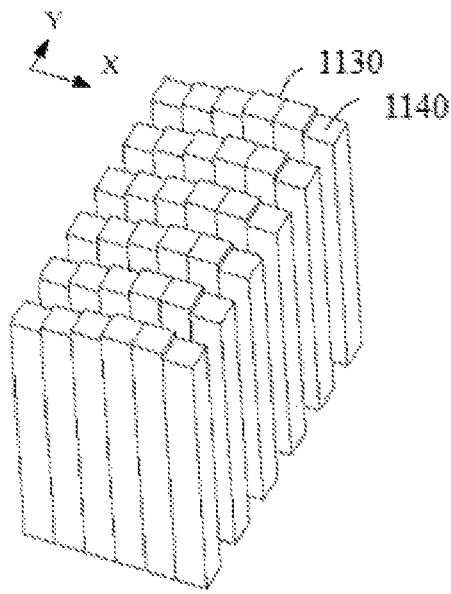
Figure 11D:
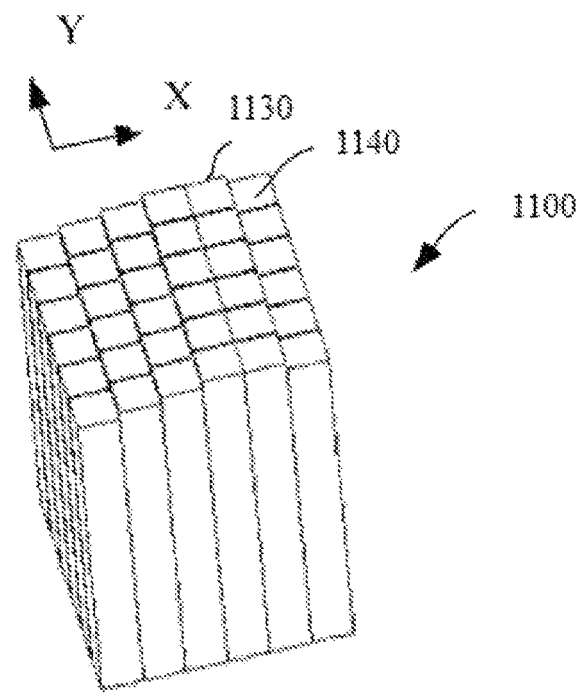
Figure 11E:
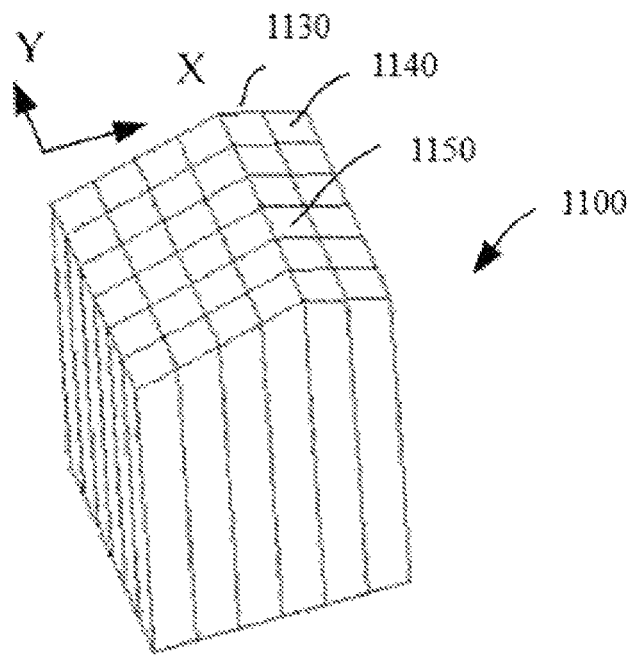

In some embodiments, the length of the scintillation crystal slice may be essentially the same as the length of the scintillation crystal array 1100 along the Y direction. As illustrated in FIG. 11A, a plurality of first scintillation crystal slices 1110 may be provided. The heights of the first scintillation crystal slices 1110 along the X direction may be designed according to the inclined plane 1150. For example, at least two of the first scintillation crystal slices 1110 along the X direction may have different heights. As illustrated in FIG. 11B, the first scintillation crystal slices 1110 may be spliced together along the X direction to form an initial scintillation crystal array 1120. Then the initial scintillation crystal array 1120 may be cut along the X direction as shown in FIG. 11C. The initial scintillation crystal array 1120 may be cut into a plurality of second scintillation crystal slices 1130. The second scintillation crystal slice 1130 may include a plurality of scintillation crystal sticks 1140. Then the second scintillation crystal slices 1130 may be spliced together along the Y direction as shown in FIG. 11D. In FIG. 11E, the spliced scintillation crystal array 1100 may be processed to form the inclined plane 1150. In some embodiments, the processing method may include grinding, cutting, polishing, cleaning, carving, or the like, or any combination thereof.

FIG. 12A through FIG. 12E illustrate an exemplary process for making a scintillation crystal array 1200 according to some embodiments of the present disclosure. The scintillation crystal array 1200 may include a plurality of first scintillation crystal slices 1210, a plurality of second scintillation crystal slices 1230, a plurality of scintillation crystal sticks 1240. The scintillation crystal array 1200 may have an inclined plane 1250.

Figure 12A:
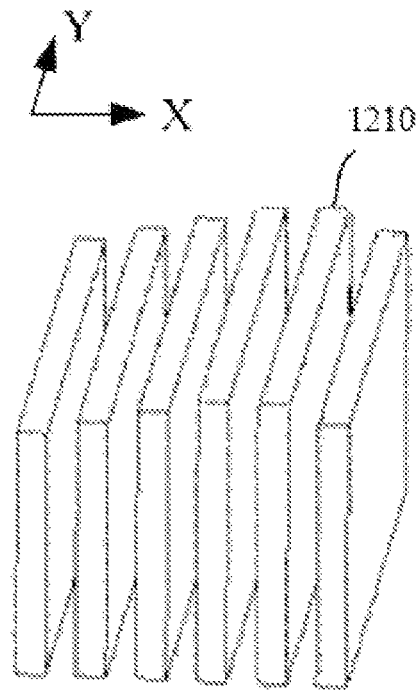
FIG. 12A-FIG. 12E illustrate an exemplary process for making a scintillation crystal array according to some embodiments of the present disclosure.
Figure 12B:
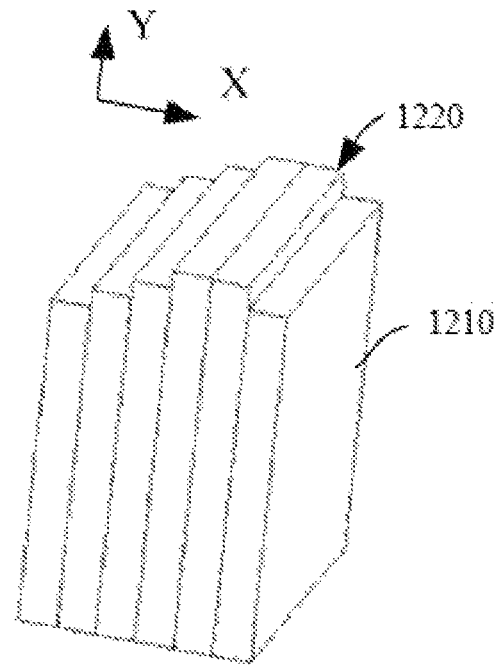
Figure 12C:
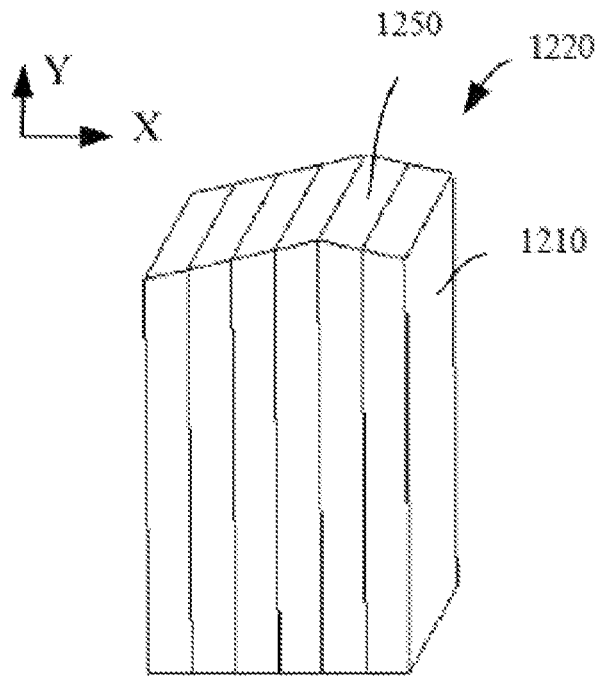
Figure 12D:
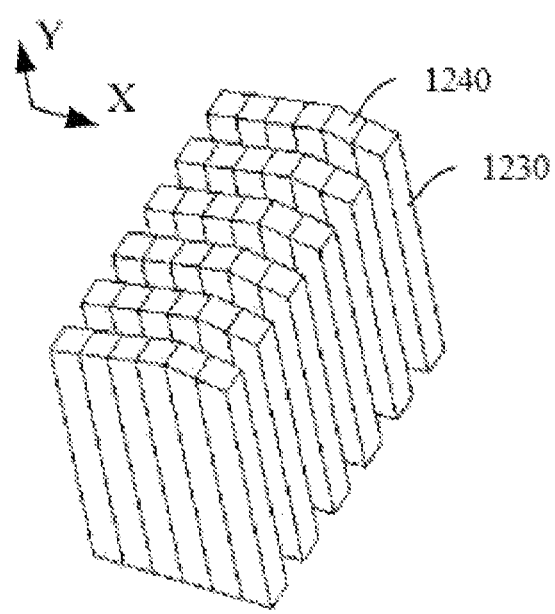
Figure 12E:
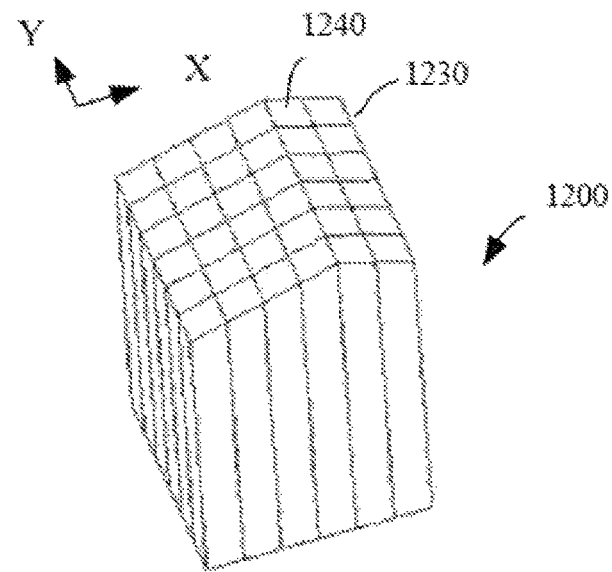

As illustrated in FIG. 12A, a plurality of first scintillation crystal slices 1210 may be provided. The heights of the first scintillation crystal slices 1210 along the X direction may be designed according to the inclined plane 1250. For example, at least two of the first scintillation crystal slices 1210 along the X direction may have different heights. As illustrated in FIG. 12B, the first scintillation crystal slices 1210 may be spliced together along the X direction to form an initial scintillation crystal array 1220. Then the initial scintillation crystal array 1220 may be processed to form the inclined plane 1250 as shown in FIG. 12C. In some embodiments, the processing method may include grinding, cutting, polishing, cleaning, carving, or the like, or any combination thereof. The initial scintillation crystal array 1220 may be cut into a plurality of second scintillation crystal slices 1230 along the X direction as shown in FIG. 12D. The second scintillation crystal slice 1230 may include a plurality of scintillation crystal sticks 1240. As shown in FIG. 12E, the second scintillation crystal slices 1230 may be spliced together along the Y direction to form the scintillation crystal array 1200.

It should be noted that the above description is merely provided for the purposes of illustration, and not intended to limit the scope of the present disclosure. For persons having ordinary skills in the art, multiple variations and modifications may be made under the teachings of the present disclosure. For example, the number of the scintillation crystal slices or the scintillation crystal sticks may be selected according to specific scenarios. As another example, the shape of the scintillation crystal slices or the scintillation crystal sticks may be different according to specific scenarios. For still another example, the splicing process may use the methods described elsewhere in the present disclosure. However, those variations and modifications do not depart from the scope of the present disclosure.

Figure 13:
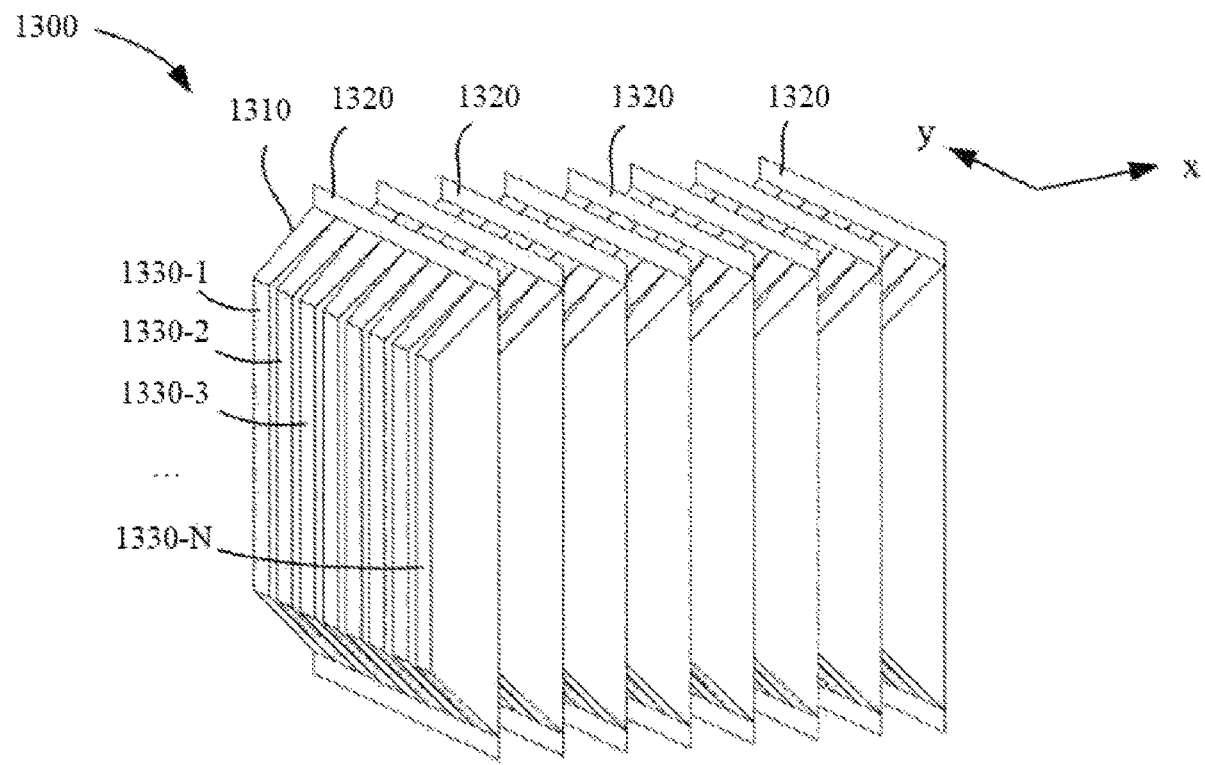
FIG. 13 is a diagram depicting a detector according to some embodiments of the present disclosure.

FIG. 13 is a diagram depicting a detector 1300 according to some embodiments of the present disclosure. The detector 1300 may be used in the imaging system 100. The imaging system 100 may be a single modality imaging system, e.g., a Digital Subtraction Angiography (DSA) system, a Magnetic Resonance Angiography (MRA) system, a Computed Tomography Angiography (CTA), a Positron Emission Tomography (PET) system, a Single Photon Emission Computed Tomography (SPECT) system, a Computed Tomography (CT) system, a Digital Radiography (DR) system, etc. In some embodiments, the imaging system may be a multi-modality imaging system, e.g., a Computed Tomography-Positron Emission Tomography (CT-PET) system, a Positron Emission Tomography-Magnetic Resonance Imaging (PET-MM) system, a Single Photon Emission Computed Tomography-Positron Emission Tomography (SPECT-PET) system, a Digital Subtraction Angiography-Magnetic Resonance Imaging (DSA-MR) system, etc. As shown in the figure, the detector 1300 may include a scintillation crystal array 1310 and an avalanche photodiode array 1320.

In some embodiments, the scintillation crystal array 1310 may include one or more scintillation crystal sticks disposed in different rows and columns. For illustration purposes, the rows may be parallel to the X direction and the columns may be parallel to the Y direction in FIG. 13. Merely by way of example, in a column of the scintillation crystal array 1310, it may include scintillation crystal sticks 1330-1, 1330-2, 1330-3, . . . , 1330-N, wherein N may be an integer. The scintillation crystal stick may include a top surface, a bottom surface, and a side surface. The bottom surface may be opposite to the top surface. The side surface may be between the bottom surface and the top surface.

In some embodiments, the avalanche photodiode array 1320 may include one or more avalanche photodiodes. The avalanche photodiode array 1320 may be of a shape of a piece, a film, a slice, a flake, a stick, a block, or the like, or any combination thereof. In some embodiments, the avalanche photodiode array 1320 may be coupled to one or more scintillation crystal sticks. For example, one piece of the avalanche photodiode array 1320 may be connected with a column of the scintillation crystal array 1310 as shown in FIG. 13. In some embodiments, the avalanche photodiode array 1320 may include one or more micro circuit units (not shown in the figure). The micro circuit units may be linked with each other in a parallel connection or a series connection. In some embodiments, the micro circuit unit may further include an avalanche photodiode and a quenching resistor.

Figure 14A:
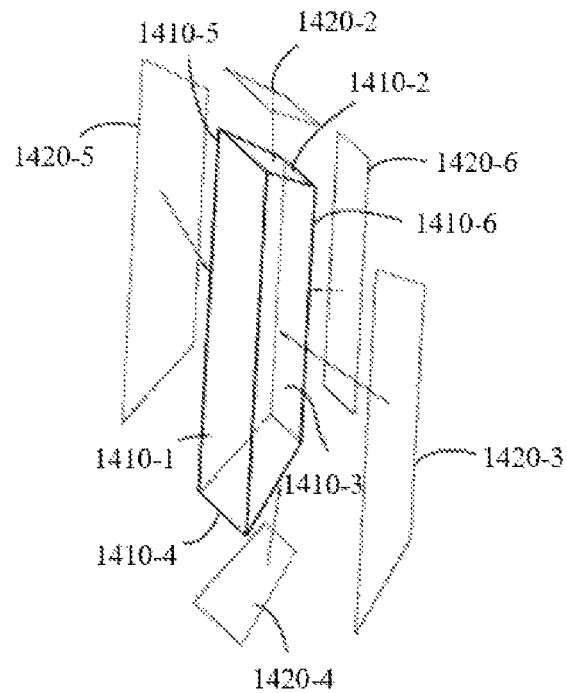
FIG. 14A-FIG. 14C illustrate an exemplary scintillation crystal stick according to some embodiments of the present disclosure.
Figure 14B:
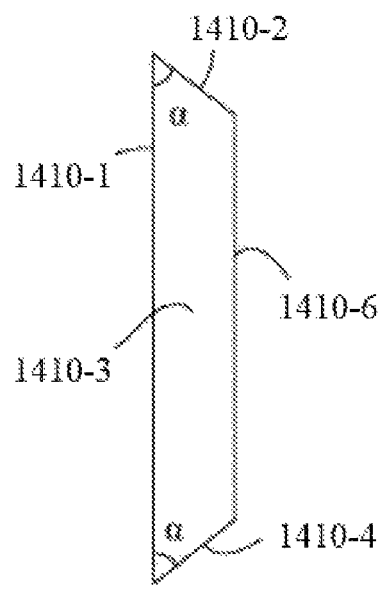
Figure 14C:
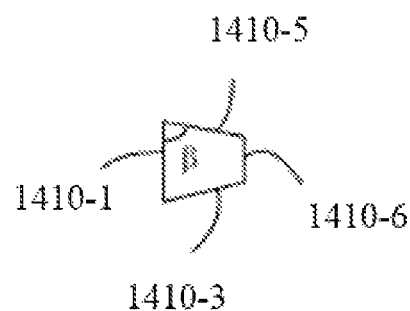

FIG. 14A through FIG. 14C illustrate an exemplary scintillation crystal stick according to some embodiments of the present disclosure. As shown in FIG. 14A, a scintillation crystal stick may include one or more surfaces 1410 and one or more reflective films 1420. The surfaces 1410 may include a coupling surface 1410-1, one or more adjacent surfaces (e.g., 1410-2, 1410-3, 1410-4, and 1410-5) close to the coupling surface 1410-1, and a parallel surface 1410-6 that is essentially parallel to the coupling surface 1410-1. The coupling surface 1410-1 may be configured to couple with an avalanche photodiode array 1320. In some embodiments, the coupling surfaces of the scintillation crystal sticks in one row or column may align in a same plane. The reflective films 1420 may decrease the transmission loss of visible light generated by γ photons. The reflective films 1420 may include a reflective film 1420-2, 1420-3, 1420-4, 1420-5, and 1420-6. In some embodiments, the reflective films may be made by a material having a certain light reflectivity. Merely for illustration purposes, the materials may include gold, silver, aluminum, copper, chromium, palladium, silicon, titanium, or the like, or an alloy thereof, or any combination thereof.

As shown in FIG. 14B, an angle α between the coupling surface 1410-1 and adjacent surface 1410-2 or 1410-4 may be no more than 90°, e.g., $\alpha \leq 90°$. For instance, a may be set between 30° and 90°, or between 45° and 90°. Merely by way of example, a may be set between 45° and 84°. In some embodiments, the angle between the coupling surface 1410-1 and the adjacent surface 1410-2 may be different from the angle between the coupling surface 1410-1 and the adjacent surface 1410-6. As shown in FIG. 14C, an angle β between the coupling surface 1410-1 and the adjacent surface 1410-3 or 1410-5 may be no more than 90°, e.g., $\beta \leq 90°$. For instance, β may be set between 60° and 90°, or between 80° and 90°. Merely by way of example, β may be set between 87° and 88°. In some embodiments, the angle between the angle between the coupling surface 1410-1 and the adjacent surface 1410-3 may be different from the angle between the coupling surface 1410-1 and the adjacent surface 1410-5. It should be noted that the values of the angle α and the angle β are merely for illustration purposes, and not intended to limit the scope of the present disclosure. For persons having ordinary skills in the art, multiple variations and modifications may be made under the teachings of the present disclosure. For example, the angle α and/or the angle β may be assigned a smaller value to decrease the reflecting function by the scintillation crystal stick.

Figure 15A:
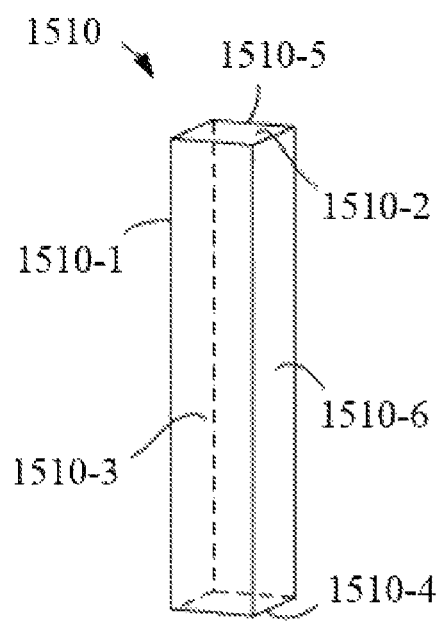
FIG. 15A and FIG. 15B illustrate an exemplary process for manufacturing a scintillation crystal stick according to some embodiments of the present disclosure.
Figure 15B:
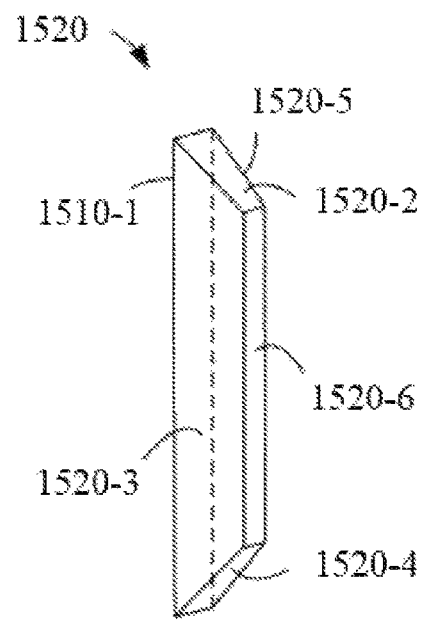

FIG. 15A and FIG. 15B illustrate an exemplary manufacture process of a scintillation crystal stick according to some embodiments of the present disclosure. As shown in FIG. 15A, a scintillation crystal block 1510 having the shape of a cuboid may be provided. The shape of the scintillation crystal block 1510 may be a cuboid, a cube, a sphere, or another regular or irregular shape. In the embodiments as illustrated in FIG. 15A, the scintillation crystal block 1510 may include a top surface 1510-2, a bottom surface 1510-4, and one or more side surfaces (e.g., 1510-1, 1510-3, 1510-5, and 1510-6). In some embodiments, the ratio of the length of a side surface to the length of the top surface or the bottom surface may be no less than 5:1. Any one of the side surfaces may be selected as a coupling surface. For illustration purposes, the side surface 1510-1 may be a coupling surface. Then one or more of the other surfaces including 1510-3, 1510-5, and 1510-6 that are adjacent and/or opposite to the side surface 1510-1 may be processed. Exemplary processing methods may include cutting, grinding, eroding, surface treating, or the like, or any combination thereof.

As shown in FIG. 15B, a scintillation crystal stick 1520 may be generated. Merely by way of example, the angle between the coupling surface 1510-1 and the top surface 1520-2 or the bottom surface 1520-4 may be assigned a value between 45° and 84°, and the angle between the coupling surface 1510-1 and side surface 1520-3 or side surface 1520-5 may be assigned a value between 87° and 88°. Then the reflective films may be disposed on the surfaces (except the coupling surface 1510-1), e.g., the top surface 1520-2, the bottom surface 1520-4, the side surface 1520-3, the side surface 1520-5, and/or the side surface 1520-6 of the scintillation crystal stick 1520. Exemplary disposing methods may include gluing, spraying, physical vapor deposition (PVD), chemical vapor deposition (CVD), or the like, or any combination thereof. PVD may include evaporating, sputtering, molecular beam epitaxy (MBE), etc. In some embodiments, one or more scintillation crystal sticks 1520 may be assembled together in one or more columns, where the coupling surfaces of all scintillation crystal sticks in one column may be set in essentially a same plane, and an avalanche photodiode array may be coupled to the coupling surfaces. One or more of the scintillation crystal sticks may be installed in a scintillation crystal array (as shown in FIG. 13).

Figure 16:
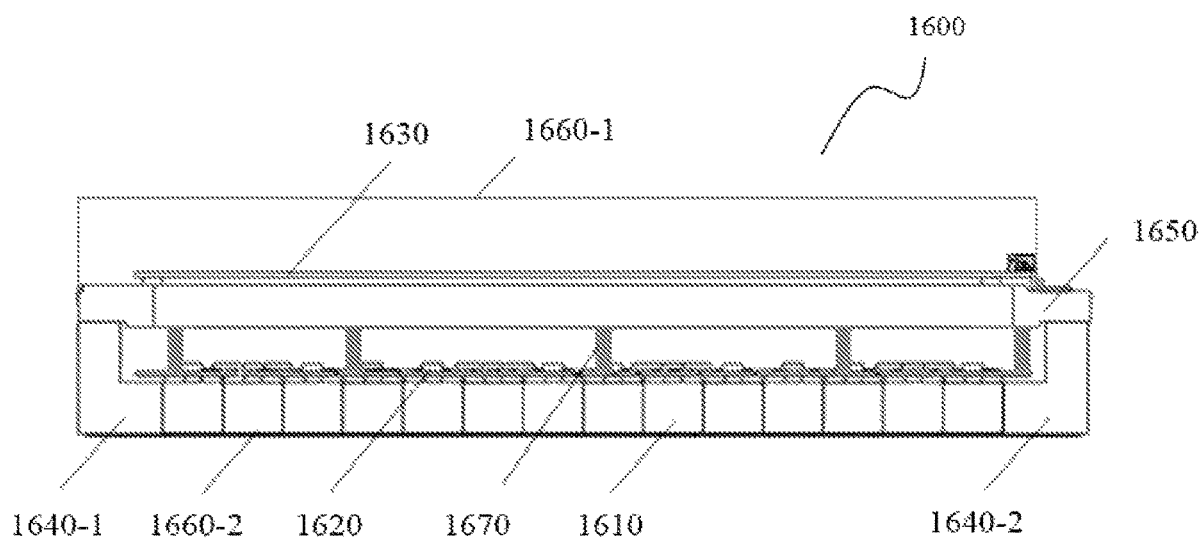
FIG. 16 is a diagram depicting a detector according to some embodiments of the present disclosure.

FIG. 16 is a diagram depicting a detector 1600 according to some embodiments of the present disclosure. The detector 1600 may be used in the imaging system 100. The imaging system 100 may be a single modality imaging system, e.g., a Digital Subtraction Angiography (DSA) system, a Magnetic Resonance Angiography (MRA) system, a Computed Tomography Angiography (CTA), a Positron Emission Tomography (PET) system, a Single Photon Emission Computed Tomography (SPECT) system, a Computed Tomography (CT) system, a Digital Radiography (DR) system, etc. In some embodiments, the imaging system may be a multi-modality imaging system, e.g., a Computed Tomography-Positron Emission Tomography (CT-PET) system, a Positron Emission Tomography-Magnetic Resonance Imaging (PET-MM) system, a Single Photon Emission Computed Tomography-Positron Emission Tomography (SPECT-PET) system, a Digital Subtraction Angiography-Magnetic Resonance Imaging (DSA-MR) system, etc. For illustration purposes, a detector used in PET may be described below as exemplary embodiments and not intended to limit the scope of the present disclosure. As shown in the figure, the detector 1600 may include a scintillation crystal array 1610, a photodetector array 1620, a circuit board 1630, a supporting block 1640, a supporting board 1650, and a shielded shell 1660.

In some embodiments, the scintillation crystal array 1610 may include one or more scintillation crystal sticks in a one-dimensional arrangement, a two-dimensional arrangement, or a three-dimensional arrangement. In the embodiments of the one-dimensional array, the scintillation crystal sticks may be disposed in a line. For example, the array may be 1 xN, wherein N may be an integer. In the embodiments of the two-dimensional array, the scintillation crystal sticks may be disposed in both horizontal and vertical directions. For example, the array may be MXN, wherein M and/or N may be an integer.

In some embodiments, the photodetector array 1620 may be configured to absorb optical energy and convert it to electrical energy. The photodetector array 1620 may be a photodiode, a PIN photodiode, an avalanche photodiode, a phototransistor, a metal-semiconductor-metal (MSM) photodetector, a photomultiplier, a pyroelectric photodetector, a thermal detector, or the like, or any combination thereof, or any photodetector as described elsewhere in the present disclosure or known in the art. The photodetector array 1620 may be optically coupled with the scintillation crystal array 1610 and be fixed on one or more circuit boards 1630. In some embodiments, the circuit board 1630 may be a printed circuit board (PCB).

In some embodiments, the supporting block 1640 may include two parts, a supporting block 1640-1 and a supporting block 1640-2. The supporting blocks 1640-1 and 1640-2 may be disposed at the two opposite ends of the scintillation crystal array 1610. For example, the supporting block 1640 may be glued with the scintillation crystal array 1610 as shown in FIG. 16. In some embodiments, the supporting block 1640-1 and the supporting block 1640-2 may be connected with each other though the supporting board 1650. The supporting board 1650 may be a flat board scalable in the horizontal direction and the vertical direction. The supporting board 1650 may be disposed between the photodetector array 1620 and the circuit board 1630. The undersurface of the supporting board 1650 may face the photodetector array 1620. The upper surface of the supporting board 1650 may face the circuit board 1630. In some embodiments, there may be a first location structure (not shown in the figure) on the supporting block 1640 or the supporting board 1650 configured to align the photodetector array 1620 on the scintillation crystal array 1610. In some embodiments, there may also be a second location structure (not shown in the figure) on the supporting block 1640 or the supporting board 1650 configured to fix the detector 1600 on an imaging scanner.

In some embodiments, one or more detectors 1600 may be encircled into a ring. The axis line of the ring may be coincided with the axis line of the scanner 100 of the imaging system 100. In some embodiments, the distance of the supporting board 1650 from the axis line may be less than the distance of the circuit board 1630.

In some embodiments, the detector 1600 may also include a shielded shell 1660. The shielded shell 1660 may be configured to contain the scintillator crystal array 1610, the photodetector array 1620, the circuit board 1630 and the supporting board 1650. In some embodiments, the shielded shell 1660 may be composed of one or more shielded boards that are connected with each other. In some embodiments, the shielded shell 1660 may also be composed of one or more shielded boards that are connected with the supporting block 1640-1 and/or the supporting block 1640-2. FIG. 16 shows two exemplary shielded boards 1660-1 and 1660-2. Exemplary materials of the shielded board 1660 may include aluminum, carbon fiber, etc. As shown in the figure, two ends of the shielded board 1660-2 may be attached to the supporting block 1640-1 and/or the supporting block 1640-2 in a non-detachable manner or a detachable manner. The non-detachable attachment may be achieve by way of, for example, cutting, casting, welding, lithographic micromachining, stacking, 3D printing, or the like, or any combination thereof. The detachable attachment may be achieved by way of, for example, plugging, riveting, screwing, interlocking, or the like, or any combination thereof. The shielded board 1660-1, 1660-2, and the supporting block 1640 may provide support to the scintillation crystal array 1610.

In some embodiments, the space in the shielded shell 1660 may be divided into a first cavity and a second cavity. In some embodiments, the scintillation crystal array 1610 and the photodetector array may be disposed in the first cavity, and the circuit board 1630 may be disposed in the second cavity. In some embodiments, the circuit board 1630 may be fixed on the supporting board 1650 or the shielded shell 1660.

In some embodiments, the first cavity may include a first space used as a passage for a cooling medium, and the second cavity may include a second space used as a passage for a cooling medium. In some embodiments, the first space and the second space may be connected with each other through a ventilation hole (not shown in the figure). The ventilation hole may be disposed on the supporting board 1650 or the supporting block 1640. In some embodiments, the imaging system may supply the cooling medium to the detector 1600. After passing through the first space, the ventilation hole, and/or the second space, the cooling medium may be exhausted from the imaging system, or cooled and re-used.

In some embodiments, the detector 1600 may also include a first elastic component 1670 and a second elastic component (not shown in the figure). The first elastic component 1670 may be disposed between the supporting board 1650 and the photodetector array 1620 in an interval manner. The supporting board 1650 may exert a force onto the photodetector array 1620 through the first elastic component 1670, and tighten the connection between the supporting board 1650 and the photodetector array 1620. The second elastic component may be disposed between the supporting board 1650 and the circuit board 1630. The supporting board 1650 may exert a force onto the circuit 1630 through the second elastic component, and tighten the connection of the supporting board 1650 and the circuit board 1630. The first and/or the second elastic component may be a spring, an elastic cushion, an elastic board, or the like, or any combination thereof. The first elastic component and the second elastic component may have thermal conductance, for example, they may be made by thermal conductive materials.

In some embodiments, there may be a cooling channel on the supporting board 1650. In these embodiments, the supporting board 1650 may include a thermal conductive material. The cooling medium may pass through the cooling channel and take away the heat of the photodetector array 1620 and the circuit board 1630.

It should be noted that the above description is merely provided for the purposes of illustration, and not intended to limit the scope of the present disclosure. For persons having ordinary skills in the art, multiple variations and modifications may be made under the teachings of the present disclosure. For example, the amount, size, shape, structure, materials, or arrangement of the scintillation crystal array, the photodetector array, the circuit board, the supporting block and the supporting board in the detector 1600 may be changed according to specific implementation scenarios. However, those variations and modifications do not depart from the scope of the present disclosure.

Figure 17:
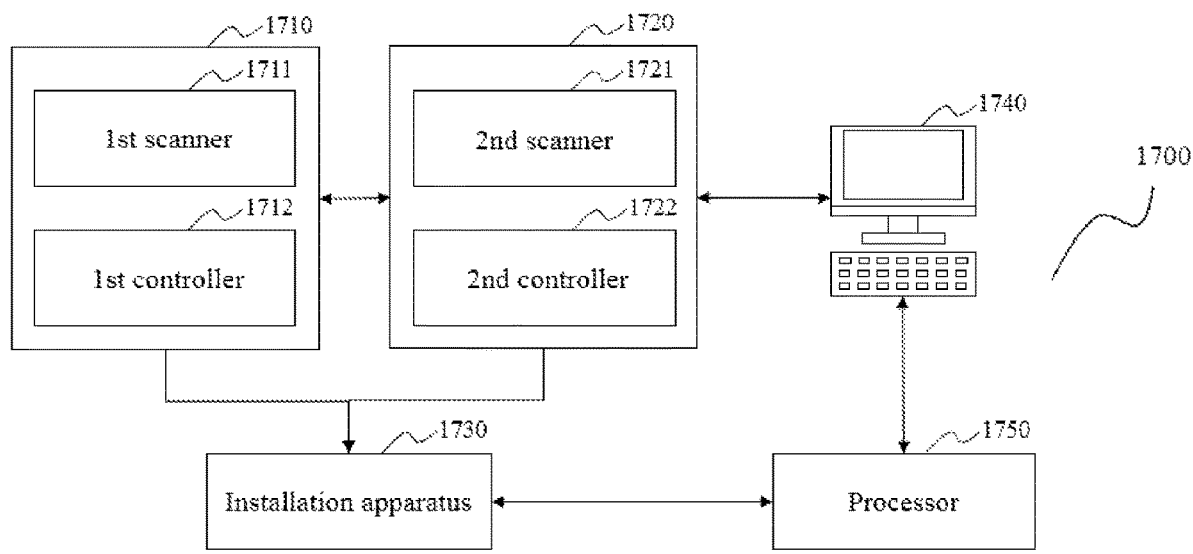
FIG. 17 is a block diagram of a multi-modality imaging system according to some embodiments of the present disclosure.

FIG. 17 is a block diagram of a multi-modality imaging system 1700 according to some embodiments of the present disclosure. It should be noted that the multi-modality imaging system 1700 described below is merely provided for illustration purposes, and not intended to limit the scope of the present disclosure. As illustrated in FIG. 17, the multi-modality imaging system 1700 may include a first modality imaging apparatus 1710, a second modality imaging apparatus 1720, an installation apparatus 1730, a workstation 1740, and a processor 1750. The first modality imaging apparatus 1710 may include a first scanner 1711 and a first controller 1712. The second modality imaging apparatus 1720 may include a second scanner 1721 and a second controller 1722.

The multi-modality imaging system 1700 may include a Computed Tomography-Positron Emission Tomography (CT-PET) system, a Computed Tomography-Magnetic Resonance Imaging (CT-MM) system, a Positron Emission Tomography-Magnetic Resonance Imaging (PET-MM) system, etc. In some embodiments, the multi-modality imaging system 1700 may further include a third modality imaging apparatus. The radiation used herein may include a particle ray, a photon ray, etc. The imaging system may find its applications in different fields, for example, medicine, or industry. As another example, the system may be used in internal inspection of components including, e.g., flaw detection, security scanning, failure analysis, metrology, assembly analysis, void analysis, wall thickness analysis, or the like, or any combination thereof.

The first modality imaging apparatus 1710 and/or the second modality imaging apparatus 1720 may be a Positron Emission Tomography (PET) system, a Single Photon Emission Computed Tomography (SPECT) system, a Computed Tomography (CT) system, a Digital Radiography (DR) system, or the like, or any combination thereof. The first scanner 1711 and/or the second scanner 1721 may be configured to acquire data according to scanning a subject. Merely by way of example, the first scanner 1711 and/or the second scanner 1721 may include a Positron Emission Tomography (PET) scanner, a Single Photon Emission Computed Tomography (SPECT) scanner, a Computed Tomography (CT) scanner, a Digital Radiography (DR) scanner, or the like, or any combination thereof. In some embodiments, the first scanner 1711 and or the second 1721 may be operated by the first controller 1712 and/or the second controller 1722 to perform selected imaging sequences of a selected target area.

The installation apparatus 1730 may be configured to align the first modality imaging apparatus 1710 with the second modality imaging apparatus 1720 coaxially. In some embodiments, the installation apparatus 1730 may include a supporting block and a set of guiding blocks etc. In some other embodiments, the installation apparatus 1730 may include a center indicator and a laser device etc.

The workstation 1740 may include a terminal, a display, a database and a network. The terminal may be configured to input and/or receive data to and/or from the network, the database, the processor, the display etc. In some embodiments, the terminal may include a user input, a controller, a processor etc. The display may be configured to display data from the scanner, the processor, the terminal, the network, or the like, or any combination thereof. The display may be any displayable device. In some embodiments, the terminal and the display may be integrated as one device configured to input data, output data, display data, and control the imaging system. The database may be configured to store data relating to the imaging system. In some embodiments, the data may include a text, an image, a voice, a force, an instruction, an algorithm, a program, or the like, or any combination thereof. The network may be configured to connect one or more components of the multi-modality imaging system. Merely by way of example, the network may include a tele communications network, a Local Area Network (LAN), a Wireless Local Area Network (WLAN), a Metropolitan Area Network (MAN), a Wide Area Network (WAN), a Bluetooth, a ZigBee, a Near Field Communication (NFC), or the like, or any combination thereof.

The processor 1750 may be configured to process the data acquired from the multi-modality imaging system 1700. In some embodiments, the data may include a text, an image, a voice, a force, an instruction, an algorithm, a program, or the like, or any combination thereof. In some embodiments, the program may include some procedures provided by the installation apparatus 1730. The procedures may be configured to install and align the multi-modality imaging system 1700. In some embodiments, the instruction may include some alignment information. The alignment information may be configured to instruct the laser to transmit to the center indicator. In some embodiments, the processor 1750 may include one or more processors, one or more processing cores, one or more memories, and one or more electronics for image processing, or the like, or any combination thereof. Merely by way of example, the processor 1750 may be a Central Processing Unit (CPU), an Application-Specific Integrated Circuit (ASIC), an Application-Specific Instruction-Set Processor (ASIP), a Graphics Processing Unit (GPU), a Physics Processing Unit (PPU), a Digital Signal Processor (DSP), a Field Programmable Gate Array (FPGA), a Programmable Logic Device (PLD), a Controller, a Microcontroller unit, a Processor, a Microprocessor, an ARM, or the like, or any combination thereof. The processor may be configured to process data acquired in the terminal. In some embodiments, the processor 1750 and the workstation 1740 may be integrated as one device.

It should be noted that the above description is merely provided for the purposes of illustration, and not intended to limit the scope of the present disclosure. For persons having ordinary skills in the art, multiple variations and modifications may be made under the teachings of the present disclosure. For example, the processor 1750 and the workstation 1740 may be implemented on a cloud platform or a remote system as described elsewhere in the present disclosure. However, those variations and modifications do not depart from the scope of the present disclosure.

Figure 18:
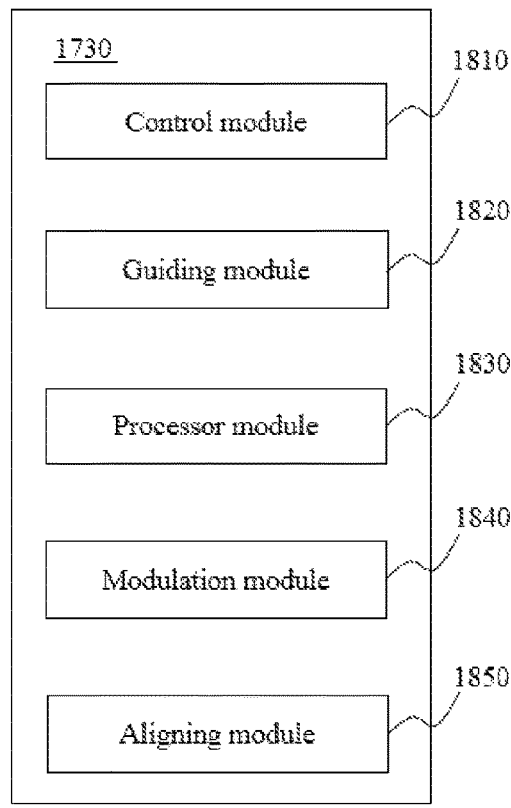
FIG. 18 is a block diagram of an installation apparatus according to some embodiments of the present disclosure.

FIG. 18 is a block diagram of the installation apparatus 1730 according to some embodiments of the present disclosure. The installation apparatus 1730 may include a control module 1810, a guiding module 1820, a processor module 1830, a modulation module 1840 and an alignment module 1850.

The control module 1810 may be configured to control the alignment process of the first modality imaging apparatus 1710 and/or the second modality imaging apparatus 1720. In some embodiments, the control module 1810 may take control of the guiding module 1820, the processor module 1830, the modulation module 1840 and/or the alignment module 1850.

The guiding module 1820 may be configured to indicate the first modality imaging apparatus 1710 aligning with the second modality imaging apparatus 1720. In some embodiments, the guiding module 1820 may include a first guiding block and a second guiding block. The first guiding block may be installed on a first housing of the first modality imaging apparatus 1710. The second guiding block may be installed on a second housing of the second modality imaging apparatus 1720. The joint of the first guiding block and the second guiding block may indicate the second modality imaging apparatus to align with the first modality imaging apparatus and install on the supporting block. In some embodiments, the guiding module 1820 may include a first center indicator and a second center indicator. In some embodiments, the first center indicator may be a rotation center indicator. The second center indicator may include a first center indicator and a second center indicator. The laser device may transmit laser through the rotation center indicator, the first center indicator, and the second center indicator to assess whether the first modality imaging apparatus and the second modality imaging apparatus align.

The processor module 1830 may be configured to identify whether the first modality imaging apparatus 1710 is coaxial with the second modality imaging apparatus 1720. In some embodiments, the processor module 1830 may calculate the center of the multi-modality imaging system 1700 for the guiding module 1820. In some embodiments, the processor module 1830 may calculate the amount of the adjustment for the modulation module 1840. In some embodiments, the processor module 1830 may identify the alignment of the multi-modality imaging system 1700 for the alignment module 1850.

The modulation module 1840 may be configured to adjust the first modality imaging apparatus 1710 so as to align with the second modality imaging apparatus 1720. In some embodiments, the modulation module 1840 may include a supporting block. The second modality imaging apparatus may be mounted on the supporting block. The number of the supporting blocks may be two or more. In some embodiments, the modulation module 1840 may include a supporting point. The number of the supporting point may be two or more. In some embodiments, the supporting points may be configured to adjust the front ends and the back ends of the multi-modality imaging system 1700 in order to align the multi-modality imaging system 1700.

The alignment module 1850 may be configured to align the first modality imaging apparatus 1710 with the second modality imaging apparatus 1720. In some embodiments, the alignment module 1850 may include an indicator. The indicator may be configured to give a feedback concerning the alignment. The feedback information may include a text, an image, a voice, a force, an instruction, an algorithm, a program, or the like, or any combination thereof.

It should be noted that the above description is merely provided for the purposes of illustration, and not intended to limit the scope of the present disclosure. For persons having ordinary skills in the art, multiple variations and modifications may be made under the teachings of the present disclosure. For example, the processor module 1840 may be displaced by a calculation module. As another example, some modules, e.g., the control module and the processing module, may be integrated as one module. However, those variations and modifications do not depart from the scope of the present disclosure.

Figure 19A:
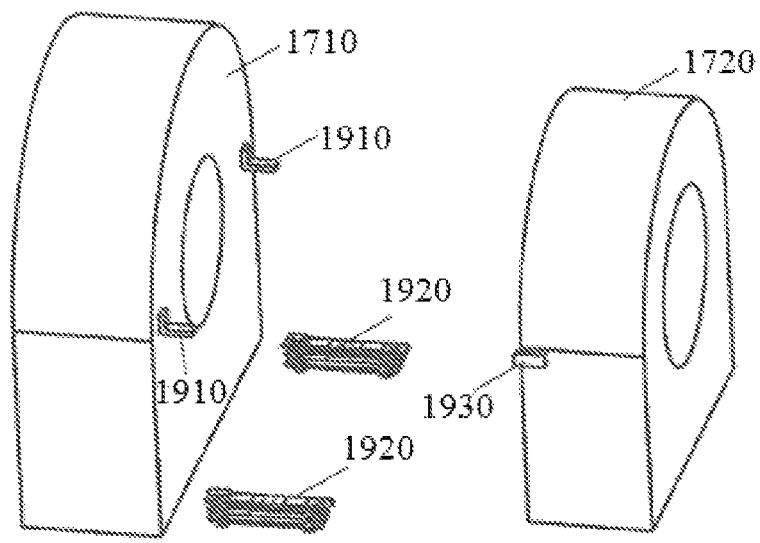
FIG. 19A and FIG. 19B illustrate an exemplary installation apparatus of a multi-modality imaging system according to some embodiments of the present disclosure.

FIG. 19A illustrates an installation apparatus of a multi-modality imaging system according to some embodiments of the present disclosure. As shown in FIG. 19A, the multi-modality imaging system may include a first modality imaging apparatus 1710, a second modality imaging apparatus 1720, and an installation apparatus. The installation apparatus may include a first guiding block 1910, a supporting block 1920, and a second guiding block 1930. The first modality imaging apparatus 1710 may include a first housing and a first scanning cavity surrounded by the first housing, where the first scanning cavity may extend along the axial direction. The second modality imaging apparatus 1720 may include a second housing and a second scanning cavity surrounded by the second housing, where the second scanning cavity may extend along the axial direction. The first guiding block 1910 may be installed on the first housing of the first modality imaging apparatus 1710. The second guiding block 1930 may be installed on the second housing of the second modality imaging apparatus 1720. The first guiding block 1910 and the second guiding block 1930 may be configured to guide the second scanning cavity of the second modality imaging apparatus 1720 to align with the first scanning cavity of the first modality imaging apparatus 1710 along the axial direction of the multi-modality imaging system. After the alignment, the axial direction of the first modalty imaging apparatus may align with the axial direction of the second modalty imaging apparatus. The axial direction of the first modalty imaging apparatus or the axial direction of the second modalty imaging apparatus may constitute the axial direction of the multi-modality imaging system. In some embodiments, the first guiding block 1910 may be installed on the outside of the first scanning cavity. The second guiding block 1930 may be installed on the outside of the second scanning cavity. In some embodiments, the first guiding block 1910 may extend beyond the front-end of the first housing or the second guiding block 1930 may extend beyond the front-end of the second housing. In some embodiments, the first guiding block 1910 may be aligned with the second guiding block 1930. Then the second modality imaging apparatus 1710 may be guided to install on the supporting block 1920.

Figure 19B:
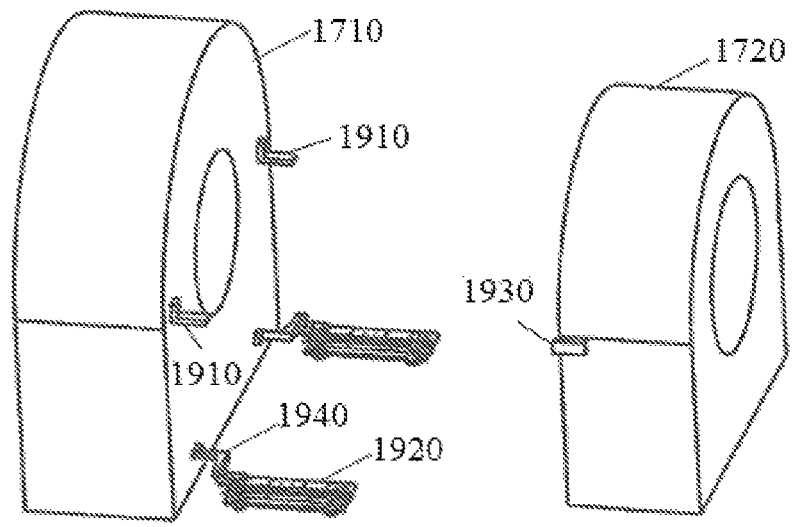

FIG. 19B illustrates an installation apparatus of a multi-modality imaging system according to some embodiments of the present disclosure. As shown in FIG. 19B, the installation apparatus may include a first guiding block 1910, a supporting block 1920, a second guiding block 1930, and a third guiding block 1940. In some embodiments, the third guiding block 1940 may have a first end and a second end. The first end of the third guiding block 1940 may be connected to the first housing of the first modality imaging apparatus 1710, and the second end of the third guiding block 1940 may be connected to the supporting block 1920. In some embodiments, the third guiding block 1940 may be configured to indicate the horizontal direction of the installation position for the supporting block 1920. The third guiding block 1940 may further be configured to determine the installation position of the second modality imaging apparatus 1720 in the horizontal direction. In some embodiments, the connection of the third guiding block 1940, the first modality imaging apparatus 1710 and the supporting block 1920 may be connected in a non-detachable manner or a detachable manner. The non-detachable connection may include, for example, cutting, casting, welding, lithographic micromachining, stacking, 3D printing, or the like, or any combination thereof. The detachable connection may include, for example, plugging, riveting, screwing, interlocking, or the like, or any combination thereof. In some embodiments, the number of the third guiding blocks 1940 and the supporting blocks 1920 may be two or more.

It should be noted that the above description is merely provided for the purposes of illustration, and not intended to limit the scope of the present disclosure. For persons having ordinary skills in the art, multiple variations and modifications may be made under the teachings of the present disclosure. For example, the number of the imaging apparatus included in the multi-modality imaging system may be three or more. As another example, the number, size, structure, shape, materials, and/or positon of the first guiding block, the second component, the third guiding block, and/or the supporting block may be variable according to different scenarios. However, those variations and modifications do not depart from the scope of the present disclosure.

Figure 20A:
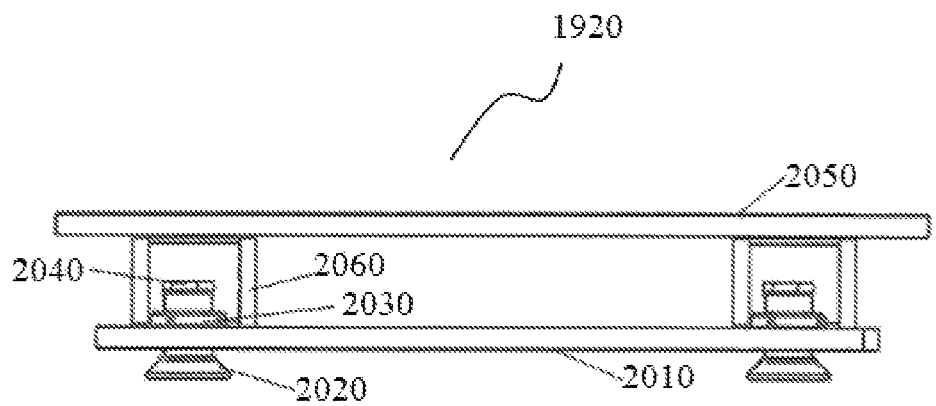
FIG. 20A and FIG. 20B illustrate an exemplary supporting block according to some embodiments of the present disclosure.

FIG. 20A illustrates a supporting block according to some embodiments of the present disclosure. As shown in FIG. 20A, the supporting block 1920 may include a supporting plate 2010 and an adjustable bolt 2020. There may be one or more screw holes on the supporting plate 2010. The adjustable bolt 2020 be disposed on the ground and pass through the screw hole of the supporting plate 2010. The adjustable bolt 2020 may adjust the distance between the first supporting plate 2010 and the ground, in order to determine the height of the supporting block 1920. A locknut 2030 may be also set on the adjustable bolt 2020. The adjustable bolt 2020 may be rotated to adjust a distance between the first supporting plate 2010 and the ground. Then the locknut 2030 may be used to lock the adjustable bolt 2020. The adjustable bolt 2020 may include a hollow cavity (not shown in the figure). A fixed bolt 2040 may pass through the hollow cavity to fix the adjustable bolt 2020 on the ground. Then the supporting block 1920 may be fixed on the ground. According to a determined relative position between the second modality imaging apparatus 1720 and the first modality imaging apparatus 1710, the position of the supporting block 1920 may be determined. The supporting block 1920 may further include a second supporting plate 2050 and a supporting lump 2060. The second supporting plate 2050 may be parallel to the first supporting plate 2010, and connected with the first supporting plate 2010 via the supporting lump 2060. The second modality imaging apparatus 1720 may be mounted on the second supporting plate 2050. The number of the adjustable bolts 2020 included in the supporting block 1920 may be one or more. Merely by way of example, each supporting block 2020 may contain four adjustable bolts 2020 that are mounted on the four corners of the first supporting plate 2010, respectively.

Figure 20B:
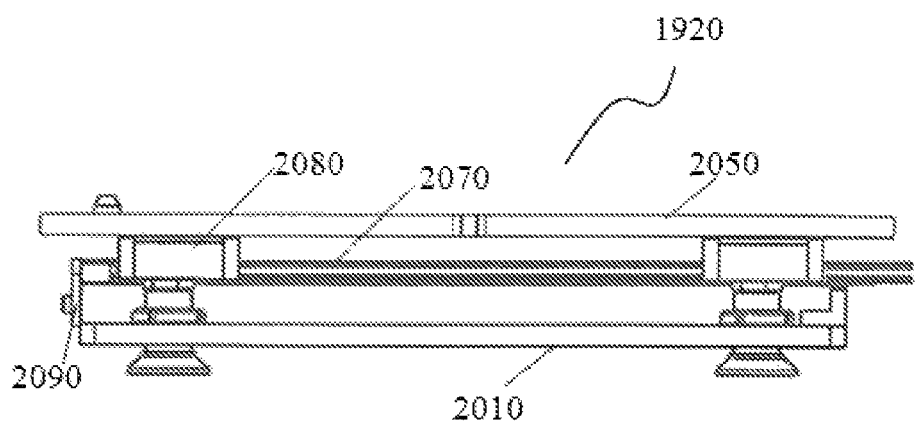

FIG. 20B illustrates a supporting block according to some embodiments of the present disclosure. As shown in FIG. 20B, the supporting block 1920 may include a guide rail 2070 and a slide lump 2080 located on the guide rail. In some embodiments, the guide rail 2070 may be mounted on the first supporting plate 2010 and connected with the first supporting plate 2010 via a fixed block 2090. The second supporting plate 2050 may be fixedly jointed with the slide lump 2080, in order to slide with the slide lump 2080 along the guide rail 2070. The second modality imaging apparatus 1720 may be mounted on the second supporting plate 2050. The second modality imaging apparatus 1720 may be detachable from the first modality imaging apparatus 1710 along the guide rail 2070. The supporting block 1920 may further include a wedge-shaped shaft (not shown in the figure). One end of the wedge-shaped shaft may be fixed on the first supporting plate 2010, and the other end of the wedge-shaped shaft may be inserted into a hole of the second supporting plate 2050. Then the second supporting plate 2050 and the slide lump 2080 may be locked on the guide rail 2070. The supporting block 1920 may further include a limit lump setting on the second supporting plate 2050. The second modality imaging apparatus 1720 may be mounted within the area surrounded by the limit lump, in order to avoid the movement relative to the second supporting plate 2050.

It should be noted that the above description is merely provided for the purposes of illustration, and not intended to limit the scope of the present disclosure. For persons having ordinary skills in the art, multiple variations and modifications may be made under the teachings of the present disclosure. For example, the number, size, structure, shape, materials, and/or positon of the components described above in the supporting block 1920 may be variable according to different scenarios. However, those variations and modifications do not depart from the scope of the present disclosure.

Figure 21A:
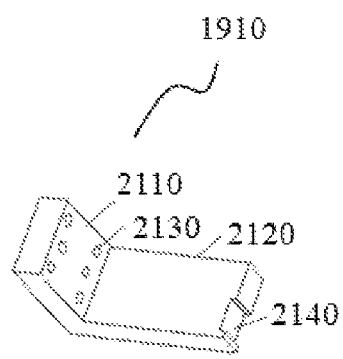
FIG. 21A is a schematic diagram of a first guiding block according to some embodiments of the present disclosure.

FIG. 21A is a structural schematic diagram of a first guiding block according to some embodiments of the present disclosure. As shown in FIG. 21A, the first guiding block 1910 may have an L-shape structure and include a first flat plate 2110 and a second flat plate 2120. In some embodiments, the first flat plate 2110 and the second flat plate 2120 may be orthogonal. The first flat plate 2110 may be set with an installation screw hole 2130. The installation screw hole 2130 may be used for installing the first guiding block 1910 on the housing of the first modality imaging apparatus 1710 at an installation position. The installation position may be measured in advance. The end of the second flat plate 2120 may be include a groove 2140. The groove 2140 may be configured to align with the second guiding block 1930 and accommodate a portion of the second modality imaging apparatus 1720 to be installed on the supporting block 1920.

Figure 21B:
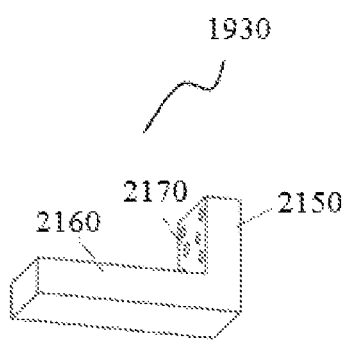
FIG. 21B is a schematic diagram of a second guiding block according to some embodiments of the present disclosure.

FIG. 21B illustrates a second guiding block according to some embodiments of the present disclosure. As shown in FIG. 21B, the second guiding block 1930 may have an L-shape structure and include a third flat plate 2150 and a fourth flat plate 2160. In some embodiments, the third flat plate 2150 and the fourth flat plate 2160 may be orthogonal. The third flat plate 2150 may be set with an installation screw hole 2170. The installation screw hole 2170 may be used for installing the second guiding block 1930 onto the housing of the second modality imaging apparatus 1720 at an installation position. The installation position may be measured in advance.

Figure 21C:
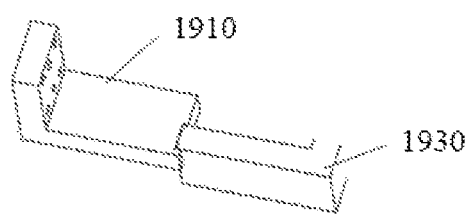
FIG. 21C is a schematic diagram of the first guiding block aligned with the second guiding block according to some embodiments of the present disclosure.

FIG. 21C illustrates an alignment of the first guiding block and the second guiding block according to some embodiments of the present disclosure. As shown in FIG. 21C, the end of the fourth flat plate 2160 of the second guiding block 1930 may be inserted in the groove 2140 of the first guiding block 1910. In some embodiments, the width of the end of the fourth flat plate 2160 may be identical to the width of the groove 2140.

In some embodiments, the end of the fourth flat plate 2140 may be set with a scale. When the end of the fourth flat plate 2160 is inserted in the groove 2140, whether the second modality imaging apparatus 1720 is mounted at the expected position in the perpendicular direction may be determined according to the indicator scale of the groove 2140. When the second modality imaging apparatus 1720 is not inserted in the expected position, the adjustable bolt 2020 may be rotated to adjust the height of the second modality imaging apparatus 1720. The locknut 2030 may be used to lock the adjustable bolt 2020 until reaching the expected position.

In some embodiments, the first guiding block 1910 may be a light emission device, and the second guiding block 1930 may be a light reception device. The light signal transmitted from the first guiding block 1910 may be received by the second guiding block 1930 if the first guiding block 1910 aligns with the second guiding block 1930.

According to the present disclosure, a method of the installation alignment by the installation apparatus 1900 used for the multi-modality imaging system is provided. The method may include the following procedures:

Step one, the first modality imaging apparatus 1710 may be installed;

Step two, the supporting block 1920 may be installed on the housing of the first modality imaging apparatus 1710 or on the ground;

Step three, the first guiding block 1910 may be installed on the housing of the first modality imaging apparatus 1710, and the second guiding block 1930 may be installed on the housing of the second modality imaging apparatus 1720;

Step four, the first guiding block 1910 and the second guiding block 1930 may guide the second scanning cavity of the second modality apparatus 1720 to align with the first scanning cavity of the first modality imaging apparatus 1710 in the axial direction, wherein the second modality imaging apparatus 1910 may be mounted on the supporting component 1920.

It should be noted that the above description is merely provided for the purposes of illustration, and not intended to limit the scope of the present disclosure. For persons having ordinary skills in the art, multiple variations and modifications may be made under the teachings of the present disclosure. For example, the first modality imaging apparatus may be mounted on the corresponding supporting block in some embodiments. However, those variations and modifications do not depart from the scope of the present disclosure.

Figure 22A:
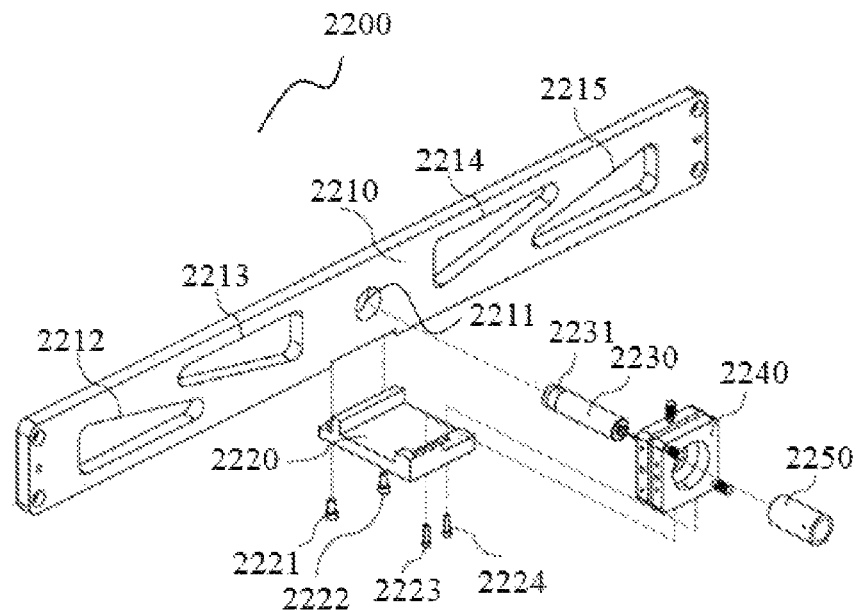
FIG. 22A is an exploded view of a CT center indicator according to some embodiments of the present disclosure.
Figure 22B:
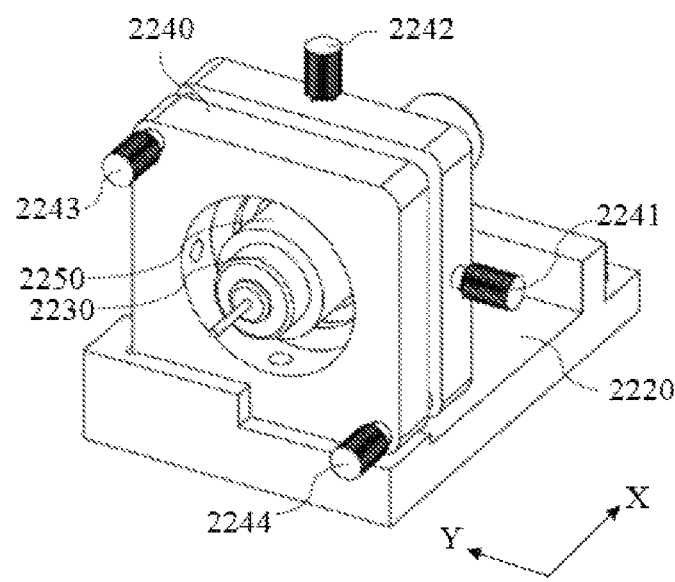
FIG. 22B is a schematic diagram of a four-dimensional adjustment platform according to some embodiments of the present disclosure.
Figure 23:
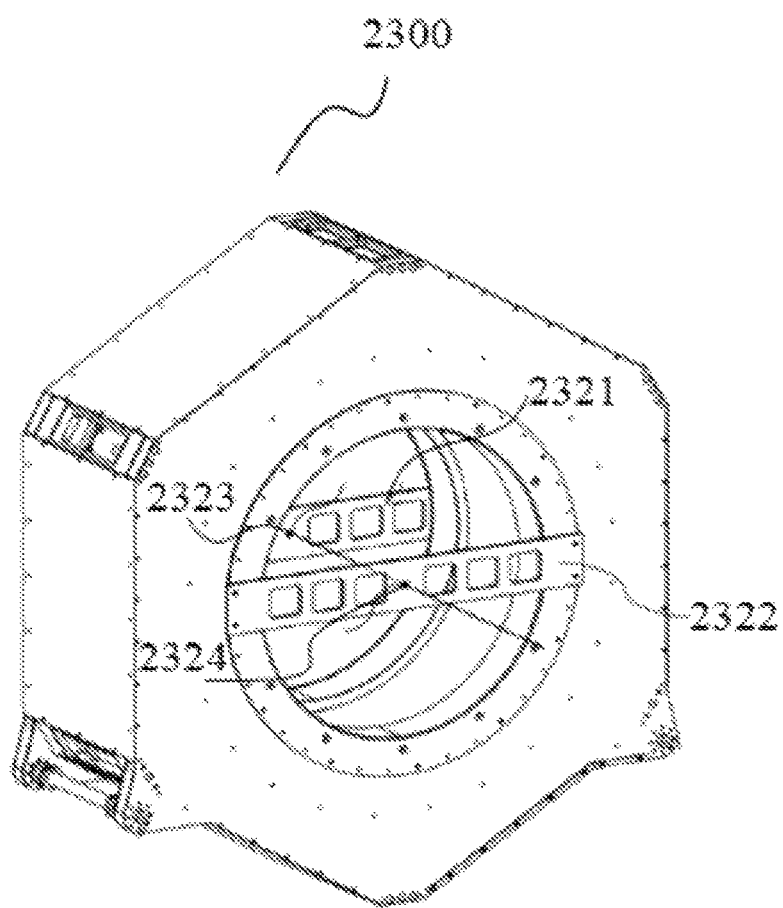
FIG. 23 illustrates a PET center indicator according to some embodiments of the present disclosure.

For illustration purposes, the first modality apparatus 1710 may be a PET apparatus and the second modality apparatus 1720 may be a CT apparatus. The PET apparatus and the CT apparatus may be coupled into a PET-CT rack. FIG. 22A is an exploded view of a CT center indicator according to some embodiments of the present disclosure. FIG. 22B is a schematic diagram of a four-dimensional adjust platform according to some embodiments of the present disclosure. FIG. 23 illustrates a PET center indicator according to some embodiments of the present disclosure. As shown in FIG. 22A, FIG. 22B, and FIG. 23, the installation alignment indicator device of the PET-CT rack may include a CT center indicator 2200 and a PET center indicator 2300. In some embodiments, the CT center indicator 2200 may be configured to indicate the rotation center of CT detector, and the PET center indicator 2300 may be configured to indicate the center of PET detector.

As shown in FIG. 22A and FIG. 22B, the CT center indicator 2200 may include a supporting plate 2210, a joint block 2220, a laser device 2230, a four-dimensional adjust platform 2240, and a laser device fixed loop 2250. The laser device 2230 may be fixed on the four-dimensional platform 2240 via the laser device fixture loop 2250. In some embodiments, the laser device 2230 may include a focus ring 2231. The focus ring 2231 may be configured to focus the laser. The four-dimensional adjust platform 2240 may include four adjusting knobs 2241-2244. The adjusting knob 2241 and/or the adjusting knob 2243 may achieve the translation of the four-dimensional adjust platform along the X direction. The adjusting knob 2242 and/or the adjusting knob 2244 may achieve translation motion of the four-dimensional adjust platform along the Y direction. The four-dimensional adjust platform 2240 may be set with the laser device 2230, and fixed on the supporting plate 2210 via the joint block 2220.

The four-dimensional adjust platform 2240 may be fixed on the reserved hickey of the joint block 2220 via a bolt 2223 and a bolt 2224. The joint block 2220 of the four-dimensional adjust platform 2240 may be fixed on the supporting plate 2210 via a bolt 2221 and a bolt 2222. Rear-end of the laser device 2230 may pass through the round hole 2211 of the center of the supporting plate 2210. In some embodiments, the round hole 2211 may be a hole which is predesigned on the supporting plate 2210. The supporting plate 2210 may further include a hole 2212, a hole 2213, a hole 2214, and a hole 2215. In some embodiments, the holes 2212-2215 may be configured to reduce the weight of the supporting plate 2211 and easy to install and disassemble.

It should be noted that the above description is merely provided for the purposes of illustration, and not intended to limit the scope of the present disclosure. For persons having ordinary skills in the art, multiple variations and modifications may be made under the teachings of the present disclosure. For example, the amount, size, shape, structure, materials, or arrangement the hole may be changed according to different scenarios. However, those variations and modifications do not depart from the scope of the present disclosure.

FIG. 23 illustrates a PET center indicator according to some embodiments of the present disclosure. As shown in FIG. 23, the PET center indicator 2300 may include a first center plate 2321, a second center plate 2322, a first center indicator 2323, and a second center indicator 2324. The first center indicator 2323 may be laid on the center of the first center plate 2321, and the second center indicator 2324 may be laid on the center of the second center plate 2322. In some embodiments, the first center indicator 2323 and the second center indicator 2324 may have an indicator plate with a cross scale, respectively. In some embodiments, the first center indicator 2323 and the second center indicator 2324 may have an indicator plate with a concentric scale, respectively. In some embodiments, the first center indicator 2323 and the second center indicator 2324 may have an indicator plate with a tiny hole in the center, respectively. Persons having ordinary skilled in the art will recognize that the present teachings are amenable to a variety of modifications and/or enhancements. For example, the first center indicator 2323 and the second center indicator 2324 may be equipped with any indicative article according to actual conditions.

It should be noted that the above description is merely provided for the purposes of illustration, and not intended to limit the scope of the present disclosure. For persons having ordinary skills in the art, multiple variations and modifications may be made under the teachings of the present disclosure. For example, the first center indicator 2323 and the second center indicator 2324 may have the indicator plate with a photo switch in the center in some embodiments. However, those variations and modifications do not depart from the scope of the present disclosure.

Figure 24:
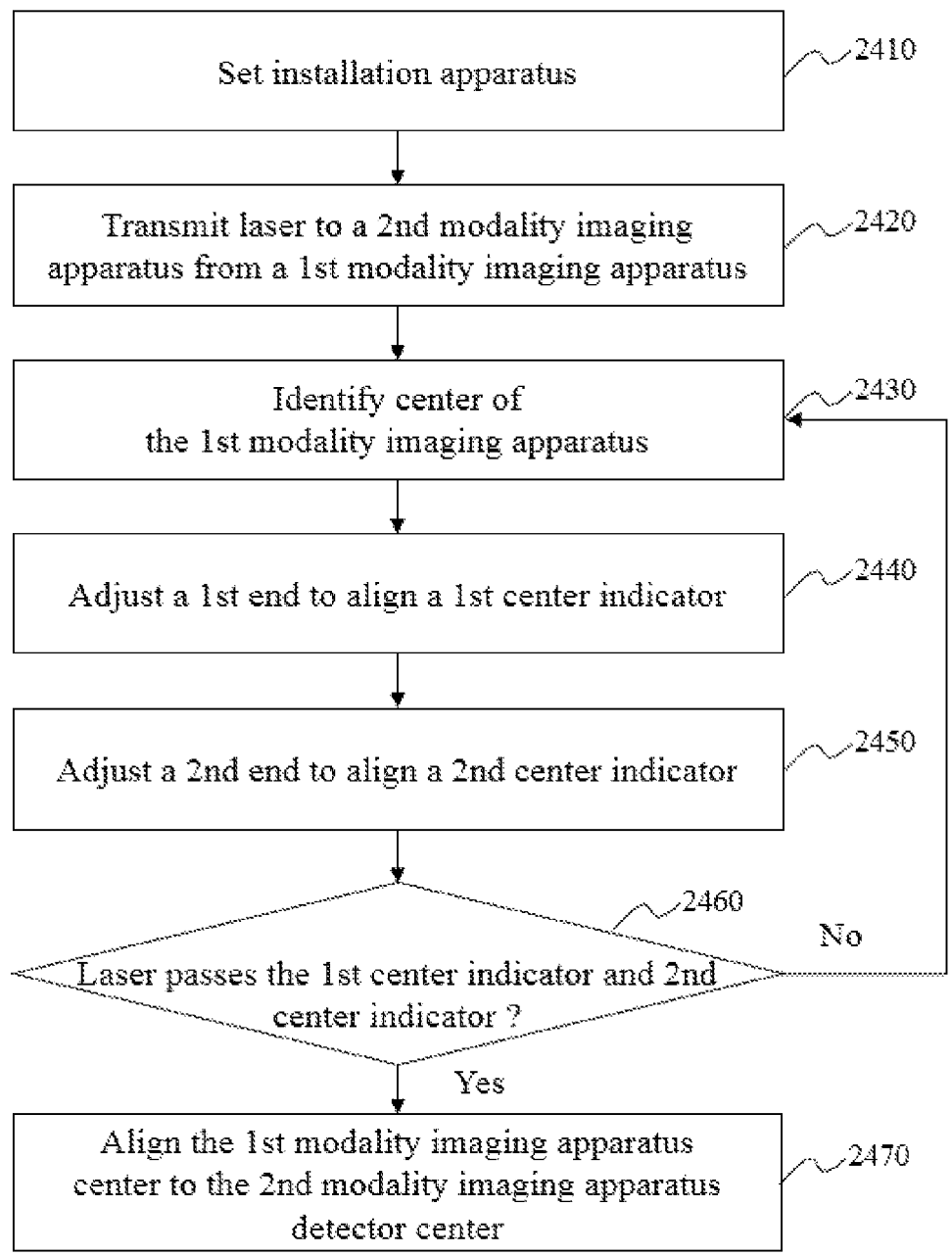
FIG. 24 illustrates an exemplary process of installation alignment in a multi-modality imaging system according to some embodiments of the present disclosure.

FIG. 24 illustrates an exemplary process of installation alignment in a multi-modality imaging system according to some embodiments of the present disclosure. It should be noted that the process described below is merely provided for illustration purposes, and not intended to limit the scope of the present disclosure.

In step 2410, the center indicator 2200 on the first modality imaging apparatus 1710 may be installed. For example, the supporting plate 2210 may be fixed on the reserved hickey of the first modality imaging apparatus 1710 via the bolt 2221 and the bolt 2222. The center indicator 2200 may be configured to indicate the center of the first modality imaging apparatus. Successively or at the same time, the second center indicator 2300 may be installed on the reserved hickey of the second modality imaging apparatus 1720. The center indicator 2300 may be configured to indicate the center of the second modality imaging apparatus.

In step 2420, a laser beam may be transmitted by the laser device 2230. In some embodiments, the laser beam may roughly focus on the center of the first modality imaging apparatus 1710. The laser device 2230 may also transmit the laser beam to a second modality imaging apparatus 1720. The second modality imaging apparatus 1720 may be set on the installation position. A laser spot may be generated on the first center plate 2321 by the laser beam transmitted from the laser device 2230. The laser spot may be moved close to the first center indicator 2323 located on the first center plate 2321. The focus ring 2231 of the laser device 2230 may be adjusted to minimize the laser spot of the first center plate 2321.

In step 2430, the center of the first modality imaging apparatus 1710 may be identified. In some embodiments, the first modality imaging apparatus 1710 may be a CT apparatus, and the CT rack may be rotated gradually by a rotation component. In some embodiments, if the laser beam do not coincide with CT rotation center exactly, the laser trajectory on the first center plate 2321 may be a circle. The adjusting knobs of the four-dimensional adjust platform 2240 may be rotated to keep the laser spot immovability.

In step 2440, a first end for aligning the first center indicator may be adjusted. In some embodiments, the second modality imaging apparatus 1720 may be a PET apparatus, and the PET rack may be moved and/or the front ends of the PET may be adjusted in order to align the laser spot with the first center indicator 2323.

In step 2450, a second end for aligning the second center indicator may be adjusted. In some embodiments, the second modality imaging apparatus may be a PET. The first center plate 2321 may be kept stationary and the first center indicator 2323 may be disassembled. The laser spot may be moved closer to the second center indicator 2324 of the second center plate 2322. The focus ring 2231 may be adjusted in order to minimize the laser spot. The back ends may be adjusted in order to align the laser spot with the second center indicator 2324. In some embodiments, the first center indicator 2323 may not be disassembled.

In step 2460, whether the laser beam passes the first center indicator and the second center indicator at the same time may be judged. In some embodiments, if the laser passes the first center indicator and the second center indicator, it may activate step 2470. In step 2470, the first modality imaging apparatus center may be aligned to the second modality imaging apparatus detector center. If the laser does not satisfy the criterion of step 2460, it may return to step 2430. In some embodiments, if the laser does not satisfy the criterion of step 2460, it may return to step 2440. After step 2470, the process of the installation alignment in a multi-modality imaging system is completed.

In some embodiments, before adjusting the supporting point of the front ends or the back ends in the second modality imaging apparatus, the rotation center of the first modality imaging apparatus may be reconfirmed. If the position of the laser spot is immovability, it may indicate that the laser spot is still on the CT rotation center. If the laser trajectory on the back center plate is a circle during the rotating of the CT rotation component, it may be necessary to adjust the adjusting knobs of the four-dimensional adjust platform 2240, in order to make sure the laser spot keeps immovability during the rotating of the CT.

It should be noted that the above description is merely provided for the purposes of illustration, and not intended to limit the scope of the present disclosure. For persons having ordinary skills in the art, multiple variations and modifications may be made under the teachings of the present disclosure. In some embodiments, the order of some steps may be exchanged. For example, the process of step 2460 may return to step 2450 instead of step 2430 or step 2440. However, those variations and modifications do not depart from the scope of the present disclosure.

Having thus described the basic concepts, it may be rather apparent to those skilled in the art after reading this detailed disclosure that the foregoing detailed disclosure is intended to be presented by way for example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "block," "module," "apparatus," "unit," "component," "device," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution—e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities of ingredients, properties such as molecular weight, reaction conditions, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. An imaging system having a first modality imaging apparatus, the first modality imaging apparatus having a detector comprising:
    a scintillator unit;
    a photodetector unit;
    a circuit unit;
    two first supporting blocks fixed on two opposite ends of the scintillator unit; and
    a shielded shell configured to contain the scintillator unit, the photodetector unit, and the circuit unit, wherein the shielded shell is composed of two shielded boards, each of the two shielded boards including a respective first end and a respective second end, each of the first ends being attached to one first supporting block of the two first supporting blocks, and each of the second ends being attached to the other first supporting block of the two first supporting blocks.

2. The imaging system of claim 1, wherein the detector further comprises:
    a supporting board disposed between the photodetector unit and the circuit unit, wherein the two first supporting blocks are directly connected with two opposite ends of the supporting board.

3. The imaging system of claim 2, wherein the supporting board comprises a ventilation hole through the supporting board.

4. The imaging system of claim 3, wherein the supporting board segments the shielded shell into a first cavity and a second cavity, the scintillator unit and the photodetector unit are disposed in the first cavity, and the circuit unit is disposed in the second cavity.

5. The imaging system of claim 4, wherein
    the first cavity includes a first space between the photodetector unit and the supporting board, the photodetector unit and the supporting board being spaced apart by at least the first space, and
    the second cavity includes a second space.

6. The imaging system of claim 5, wherein the first space and the second space are configured to accommodate a cooling medium, and the ventilation hole connects the first space and the second space to allow the cooling medium to flow between the first space and the second space.

7. The imaging system of claim 2, wherein the detector further comprises:
    a first elastic component disposed between the supporting board and the circuit unit.

8. The imaging system of claim 7, wherein the detector further comprises:
    a second elastic component disposed between the supporting board and the photodetector unit.

9. The imaging system of claim 8, wherein the first elastic component or the second elastic component has thermal conductance.

10. The imaging system of claim 8, wherein the first elastic component or the second elastic component is a spring, an elastic cushion, or an elastic board.

11. The imaging system of claim 8, wherein the supporting board and the photodetector unit are connected by the second elastic component.

12. The imaging system of claim 2, wherein the detector further comprises a first location structure, the first location structure being on the two first supporting blocks or the supporting board and being configured to align the photodetector unit on the scintillator unit.

13. The imaging system of claim 2, wherein the detector further comprises a second location structure, the second location structure being on the two first supporting blocks or the supporting board and being configured to fix the detector on the first modality imaging apparatus.

14. The imaging system of claim 2, wherein the detector is configured to encircle a ring having an axis, and a distance between the supporting board and the axis of the ring is less than a distance between the circuit unit and the axis of the ring.

15. The imaging system of claim 1, wherein each of the first ends of the two shielded boards is attached to one first supporting block of the two first supporting blocks in a detachable manner.

16. The imaging system of claim 15, wherein each of the second ends of the two shielded boards is attached to the other first supporting block of the two first supporting blocks in the detachable manner.

17. The imaging system of claim 1, wherein the scintillator unit includes one or more scintillation crystal sticks in a one-dimensional arrangement, a two-dimensional arrangement, or a three-dimensional arrangement.

18. The imaging system of claim 17, wherein the photodetector unit includes one or more avalanche photodiodes, and one piece of the photodetector unit is connected with a column of the scintillator unit.

19. The imaging system of claim 1, wherein the two first supporting blocks are glued with two ends of the scintillator unit respectively.

20. The imaging system of claim 1, further comprising:
    a second modality imaging apparatus; and
    an installation apparatus configured to align the first modality imaging apparatus with the second modality imaging apparatus.

* * * * *